(12) United States Patent
Miura et al.

(10) Patent No.: US 8,895,692 B2
(45) Date of Patent: Nov. 25, 2014

(54) FUSED RING COMPOUND AND METHOD FOR PRODUCING SAME, POLYMER, ORGANIC THIN FILM CONTAINING THOSE, AND ORGANIC THIN FILM DEVICE AND ORGANIC THIN FILM TRANSISTOR COMPRISING SUCH ORGANIC THIN FILM

(75) Inventors: Masahiro Miura, Suita (JP); Tetsuya Satoh, Suita (JP); Hiroyuki Watanabe, Suita (JP); Masato Ueda, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1578 days.

(21) Appl. No.: 12/282,071

(22) PCT Filed: Feb. 2, 2007

(86) PCT No.: PCT/JP2007/051811
§ 371 (c)(1),
(2), (4) Date: Oct. 27, 2008

(87) PCT Pub. No.: WO2007/105386
PCT Pub. Date: Sep. 20, 2007

(65) Prior Publication Data
US 2009/0065770 A1    Mar. 12, 2009

(30) Foreign Application Priority Data
Mar. 10, 2006 (JP) .................................. 2006-066504

(51) Int. Cl.
*C08G 75/06* (2006.01)
(Continued)

(52) U.S. Cl.
CPC ......... *H01L 51/0043* (2013.01); *H01L 51/0541* (2013.01); *H01L 51/0545* (2013.01);
(Continued)

(58) Field of Classification Search
USPC ....... 528/377, 380; 526/256; 549/43; 257/40, 257/E51.006
See application file for complete search history.

(56) References Cited

U.S. PATENT DOCUMENTS

| 4,853,090 A | 8/1989 | Daniel et al. |
| 5,646,284 A | 7/1997 | Usuki et al. |
| 2004/0167364 A1 | 8/2004 | Itahashi et al. |

FOREIGN PATENT DOCUMENTS

JP    2-015079 A    1/1990
(Continued)

OTHER PUBLICATIONS

T. Yamamoto et al., "Poly(1,10-phenanthroline-3, 8-diyl) and its derivatives. Preparation, optical and electrochemical properties, solid structure and their metal complexes", Macromolecules, vol. 36, (2003), pp. 6722-6729, (XP002519527).
(Continued)

*Primary Examiner* — Duc Truong
(74) *Attorney, Agent, or Firm* — Sughrue Mion, PLLC

(57) ABSTRACT

It is an object of the present invention to provide a fused ring compound which can exhibit sufficient charge transport properties and which has excellent solubility in a solvent. The fused ring compound according to the present invention is represented by the following general formula (1),

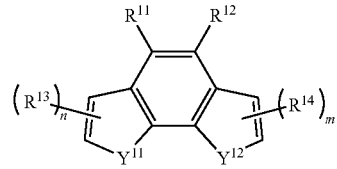

(1)

wherein $R^{11}$ and $R^{12}$ each independently represent a hydrogen atom, an alkyl group having 1 to 20 carbon atoms, an alkoxy group, an alkylthio group, an alkylamino group, an alkoxycarbonyl group, an optionally substituted aryl group having 6 to 60 carbon atoms, an optionally substituted heterocyclic group having 4 to 60 carbon atoms, or a cyano group, provided that at least one of $R^{11}$ and $R^{12}$ is not a hydrogen atom; $R^{13}$ and $R^{14}$ each independently represent a monovalent group, and n and m each independently denote an integer of 0 to 2; and $Y^{11}$ and $Y^{12}$ are each independently a divalent group comprising a sulfur atom, an oxygen atom, a nitrogen atom, a selenium atom or a tellurium atom.

3 Claims, 8 Drawing Sheets

(51) Int. Cl.
    *H01L 51/00*     (2006.01)
    *C09K 11/06*     (2006.01)
    *C07D 495/04*     (2006.01)
    *C08G 75/00*     (2006.01)
    *H01L 51/05*     (2006.01)
    *H01L 51/10*     (2006.01)

(52) U.S. Cl.
    CPC .. *C08G 2261/3223* (2013.01); *C08G 2261/122* (2013.01); *H01L 51/0036* (2013.01); *C09K 11/06* (2013.01); *C09K 2211/1458* (2013.01); *C08G 2261/3243* (2013.01); *C09K 2211/1416* (2013.01); *H01L 51/0039* (2013.01); *C08G 2261/92* (2013.01); *H01L 51/105* (2013.01); *C08G 2261/3142* (2013.01); *C07D 495/04* (2013.01)
    USPC ............. 528/377; 528/380; 526/256; 549/43; 257/40; 257/E51.006

(56) References Cited

FOREIGN PATENT DOCUMENTS

| | | |
|---|---|---|
| JP | 7-228865 A | 8/1995 |
| JP | 11-195790 A | 7/1999 |
| JP | 2000-076640 A | 3/2000 |
| JP | 2003-221579 A | 8/2003 |
| JP | 2003-530366 A | 10/2003 |
| JP | 2004-269519 A | 9/2004 |
| JP | 2004-339516 A | 12/2004 |
| JP | 2006-005036 A | 1/2006 |
| WO | 03/072581 A1 | 9/2003 |
| WO | 2004/005288 | 1/2004 |
| WO | 2005/003126 A1 | 1/2005 |
| WO | 2005/034929 A2 | 4/2005 |

OTHER PUBLICATIONS

A. Abreu et al., "Synthesis of beta-benzo[b]thienyldehydrophenylalanine derivatives by one-pot palladium-catalyzed borylation and Suzuki coupling (BSC) and metal-assisted intramolecular cylization—studies of fluorescence and antimicrobial activity", European J. Org. Chem., (2005), pp. 2951-2957, (XP002519528).

Tsuchimoto, T. et al., Easy access to aryl- and heteroaryl-annuatedacarbazoles by the indium-catalyzed reaction of 2-arylindoles with propargyl ethers, Angewandte Chemie, International Edition, 2005, vol. 44, No. 9, pp. 1336-1340.

Wiersema, Allert K. et al., Thiophene analog of fluorene. IV. Unusual behavior of a cyclopentadithiophenone in the reaction with dienophiles, Acta Chemica Scandinavica, 1947-1973, (1970), 24 (7), pp. 2653-2655.

Merlic, Craig et al., Synthesis of indolocarbazoles via sequential palladium catalyzed cross-coupling and benzannulation reactions, Tetrahedron Letters, (1997), 38 (44), pp. 7661-7664.

Z. Bao et al., "Soluble and processable regioregular poly(3-hexylthiophene) for thin film field-effect transistor applications with high mobility", Appl.Phys. Letter, 69, (1996), pp. 4108-4110.

X. Li et al., "A Highly-Stacked Organic Semiconductor for Thin Film Transistors Based on Fused Thiophenes", J. Am. Chem. Soc. 120, (1998), pp. 2206-2207.

P. Coppo et al., "Synthesis, solid state structure and polymerisation of a fully planar cyclopentadithiophene", Chem. Commun., (2003), pp. 2548-2549.

Japanese Patent Office, "Notice of Reasons for Rejection," issued in connection with Japanese Patent Application No. P2007-024498, dated Jun. 8, 2012.

Kanno et al., "Chromium-Mediated Synthesis of Polycyclic Aromatic Compounds from Halobiaryls," Organic Letters, 2005, vol. 7, No. 24, pp. 5453-5456.

Yoshida et al., "Novel Electron Acceptors Bearing a Heteroquinonoid System. 4. Syntheses, Properties, and Charge-Transfer Complexes of 2,7-Bis(dicyanomethylene)-2,7-dihydrobenzo[2,1-*b*:3,4-*b*']dithiophene, 2,7-Bis(dicyanomethylene)-2,7-dihydrobenzo[1,2-*b*:4,3-*b*']dithiophene, and 2,6-Bis(dicyanomethylene)-2,6-dihydrobenzo[1,2-*b*:4,5-*b*']dithiophene," J. Org. Chem., 1994, vol. 59, pp. 3077-3081.

Archer et al., "Electrophilic Aromatic Substitution. Part 34. Partial Rate Factors for Detritiation of Dithieno[1,2-*b*:4,3-*b*']benzene, Dithieno[1,2-*b*':3,4-*b*']benzene, and Dithieno[2,1-*b*:3,4-*b*']benzene," J. Chem. Soc. Perkin Trans, vol. II, 1983, pp. 813-819.

FUSED RING COMPOUND AND METHOD FOR PRODUCING SAME, POLYMER, ORGANIC THIN FILM CONTAINING THOSE, AND ORGANIC THIN FILM DEVICE AND ORGANIC THIN FILM TRANSISTOR COMPRISING SUCH ORGANIC THIN FILM

TECHNICAL FIELD

The present invention relates to a fused ring compound and a production method thereof, a polymer, an organic thin film including these, and an organic thin film device and organic thin film transistor including this.

BACKGROUND ART

Recently, a great deal of investigation is going into organic semiconductor materials, due to their application in various organic thin film devices, such as organic EL (electroluminescence) devices, organic film transistors, organic solar cells, and light sensors. To obtain excellent performance in such applications, the organic semiconductor material has to have high charge (electron or hole) transport properties. To obtain high charge transport properties, in the organic semiconductor material, it is important to have good molecular packing and to increase the interaction between molecules by using molecules with extended π conjugation.

From such a perspective, known organic semiconductor materials which can obtain high charge transport properties include compounds containing a dithienothiophene (Patent Document 1), compounds in which a plurality of thiophene rings are joined in a planar manner (see Non-patent Documents 1 to 3) and the like.

[Patent Document 1] Japanese Patent Laid-Open No. 2004-339516

[Non-patent Document 1] Z. Bao et al., "Appl. Phys. Lett.", 1996, 69, 4108.

[Non-patent Document 2] X. Li et al., "J. Am. Chem. Soc.", 1998, 120, 2206.

[Non-patent Document 3] P. Coppo et al., "Chem. Commun.", 2003, 2548.

DISCLOSURE OF THE INVENTION

However, although the above-described compounds used as an organic semiconductor material all have high planarity and also have excellent charge transport properties, since such compounds do not have high solubility in solvents, there are many difficulties in forming an organic thin film. Although solubility in a solvent could be increased by lowering etc. the planarity of the compounds, such a case then tends to suffer from a tendency that the charge transport properties are insufficient.

Accordingly, the present invention was created in view of such circumstances. It is an object of the present invention to provide a fused ring compound and a polymer which can exhibit sufficient charge transport properties and which have excellent solubility in a solvent. It is a further object of the present invention to provide a method for producing the fused ring compound, an organic thin film using the fused ring compound, and an organic thin film device and organic thin film transistor which include this organic thin film.

To achieve the above objects, the fused ring compound according to the present invention is characterized by being represented by the following general formula (1),

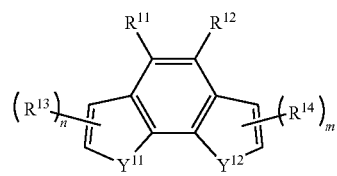

wherein $R^{11}$ and $R^{12}$ each independently represent a hydrogen atom, an alkyl group, an alkoxy group, an alkylthio group, an alkylamino group, an alkoxycarbonyl group, an optionally substituted aryl group, an optionally substituted heterocyclic group, or a cyano group, provided that at least one of $R^{11}$ and $R^{12}$ is not a hydrogen atom; $R^{13}$ and $R^{14}$ each independently represent a monovalent group, and n and m each independently denote an integer of 0 to 2, provided that when a plurality of both $R^{13}$ and $R^{14}$ are present, such groups may be the same or different; and $Y^{11}$ and $R^{12}$ are each independently a divalent group represented by the following general formula (2a), (2b), (2c), (2d), (2e), (2f), (2g), or (2h),

  (2a)

  (2b)

  (2c)

  (2d)

  (2e)

  (2f)

  (2g)

  (2h)

wherein $R^{21}$ and $R^{22}$ each independently represent a hydrogen atom or a monovalent group.

Since fused ring compounds having the above-described structure have a structure in which three aromatic ring structures are fused and the π conjugation is spread out, when such a fused ring compound forms an organic thin film or the like, the film can exhibit high charge transport properties. Further, such a fused ring compound has a structure in which a substituent has been introduced in the center of a benzene ring structure. As a result, the fused ring compound has good solubility in solvents and the like, and can be easily processed into an organic thin film and the like. Therefore, the fused ring compound according to the present invention is useful as an organic semiconductor material for forming an organic thin film in an organic thin film device.

In the above-described fused ring compound according to the present invention, $Y^{11}$ and $Y^{12}$ are preferably a divalent group represented by general formula (2a). As a result, the charge transport properties from the fused ring compound become even better. Further, such a compound has the advantages that it is relatively easy to synthesize, and can be obtained easily.

Further, $R^{11}$ and $R^{12}$ are preferably each independently an alkyl group having 1 to 10 carbon atoms, or an optionally substituted aryl group having 6 to 20 carbon atoms. As a result, the solubility of the fused ring compound in a solvent becomes even better.

Further, the polymer according to the present invention is characterized by including a monomer unit represented by the following general formula (3),

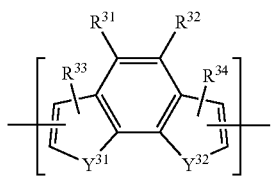

(3)

wherein $R^{31}$ and $R^{32}$ each independently represent a hydrogen atom, an alkyl group, an alkoxy group, an alkylthio group, an alkylamino group, an alkoxycarbonyl group, an optionally substituted aryl group, an optionally substituted heterocyclic group, or a cyano group, provided that at least one of $R^{31}$ and $R^{32}$ is not a hydrogen atom; $R^{33}$ and $R^{34}$ each independently represent a hydrogen atom or a monovalent group; and $Y^{31}$ and $Y^{32}$ are each independently a divalent group represented by the following general formula (4a), (4b), (4c), (4d), (4e), (4f), (4g), or (4h),

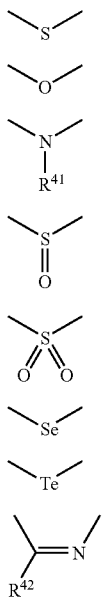

(4a)
(4b)
(4c)
(4d)
(4e)
(4f)
(4g)
(4h)

wherein $R^{41}$ and $R^{42}$ each independently represent a hydrogen atom or a monovalent group.

Since such a polymer includes the same fused ring structure as that of the above-described fused ring compound according to the present invention, the polymer not only has excellent charge transport properties, but also has excellent solubility in a solvent.

More preferably, the polymer according to the present invention further includes a repeating unit represented by the following general formula (5), $$—Ar^5—\qquad(5)$$

wherein $Ar^5$ represents an optionally substituted aromatic hydrocarbon group or an optionally substituted heterocyclic group. As a result, the charge transport properties of the polymer are even more improved.

It is especially preferable if the above $Ar^5$ is a group represented by the following general formula (6),

(6)

wherein $R^{61}$ and $R^{62}$ each independently represent a hydrogen atom or a monovalent group; $R^{61}$ and $R^{62}$ may be joined to form a ring; $Y^6$ is a divalent group represented by the following general formula (7a), (7b), (7c), (7d), (7e), (7f), (7g), (7h), or (7i), (7a)
(7b)
(7c)
(7d)
(7e)
(7f)
(7g)
(7h)
(7i)

wherein $R^{71}$, $R^{72}$, $R^{73}$ and $R^{74}$ each independently represent a hydrogen atom or a monovalent group; and $R^{73}$ and $R^{74}$ may be joined together to form a ring. As a result, the charge transport properties of the polymer are substantially improved.

More specifically, in the above-described polymer according to the present invention, $Y^{31}$ and $Y^{32}$ are preferably a divalent group represented by general formula (4a), and $Y^6$ in the group represented by general formula (6) is preferably a divalent group represented by general formula (7a). As a result, even better charge transport properties and solubility can be obtained.

Further, the method for producing the fused ring compound according to the present invention is a method which forms the fused ring compound according to the present invention well, the method being characterized by comprising reacting a compound represented by the following general formula (8a) and a compound represented by the following general formula (8b) in the presence of a base and a metal complex catalyst, to obtain a fused ring compound represented by the following general formula (8c),

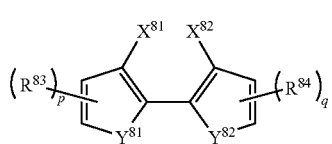
(8a)

(8b)

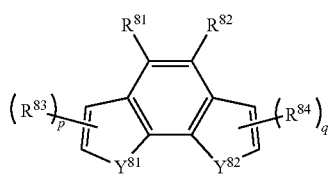
(8c)

wherein $X^{81}$ and $X^{82}$ are each independently a hydrogen atom or a halogen atom, provided that at least one of $X^{81}$ and $X^{82}$ is a halogen atom; $R^{81}$ and $R^{82}$ each independently represent a hydrogen atom, an alkyl group, an alkoxy group, an alkylthio group, an alkylamino group, an alkoxycarbonyl group, an optionally substituted aryl group, an optionally substituted heterocyclic group, or a cyano group, provided that at least one of $R^{81}$ and $R^{82}$ is not a hydrogen atom; $R^{83}$ and $R^{84}$ each independently represent a monovalent group, and p and q each independently denote an integer of 0 to 2, provided that when a plurality of both $R^{83}$ and $R^{84}$ are present, such groups may be the same or different; and $Y^{81}$ and $Y^{82}$ are each independently a divalent group represented by the following general formula (9a), (9b), (9c), (9d), (9e), (9f), (9g), or (9h),

(9a)

(9b)

(9c)

(9d)

(9e)

(9f)

(9g)

(9h)

wherein $R^{91}$ and $R^{92}$ each independently represent a hydrogen atom or a monovalent group.

In such production method, $Y^{81}$ and $Y^{82}$ are preferably a divalent group represented by general formula (9a). As a result, a fused ring compound having excellent charge transport properties can be obtained. Further, since such a compound can be relatively easily synthesized, a fused ring compound can be easily produced by using such compound.

Further, it is preferred that at least one of $X^{81}$ and $X^{82}$ is a halogen atom, and it is more preferred that both of these are halogen atoms. More specifically, it is preferred that at least one of $X^{81}$ and $X^{82}$ is an iodine atom, and it is more preferred that both of these are iodine atoms. As a result, the reaction between the compound represented by the general formula (8a) and the compound represented by the general formula (8b) occurs more easily, so that the compound represented by the general formula (8c) can be obtained even more efficiently.

The present invention further provides an organic thin film which includes the above-described fused ring compound and/or polymer according to the present invention. Since such an organic thin film includes the fused ring compound and/or polymer according to the present invention, the organic thin film has excellent charge transport properties, and is thus suitable in an organic thin film device and the like.

The present invention further provides an organic thin film device which includes the above-described organic thin film according to the present invention. As such an organic thin film device, an organic thin film transistor is preferred. Since such an organic thin film device includes the organic thin film according to the present invention which has high charge transport properties, the organic thin film device can exhibit excellent characteristics.

EFFECT OF THE INVENTION

According to the present invention, a fused ring compound and polymer can be provided which can exhibit sufficient charge transport properties, and which have excellent solubility in a solvent. Further, according to the present invention, a preferred method for producing the above-described fused ring compound can be provided. In addition, according to the present invention, an organic thin film having excellent charge transport properties obtained using the above-described fused ring compound, and an organic thin film device and organic thin film transistor including such an organic thin film, can be provided.

DESCRIPTION OF THE REFERENCE NUMERALS

Figure 1:
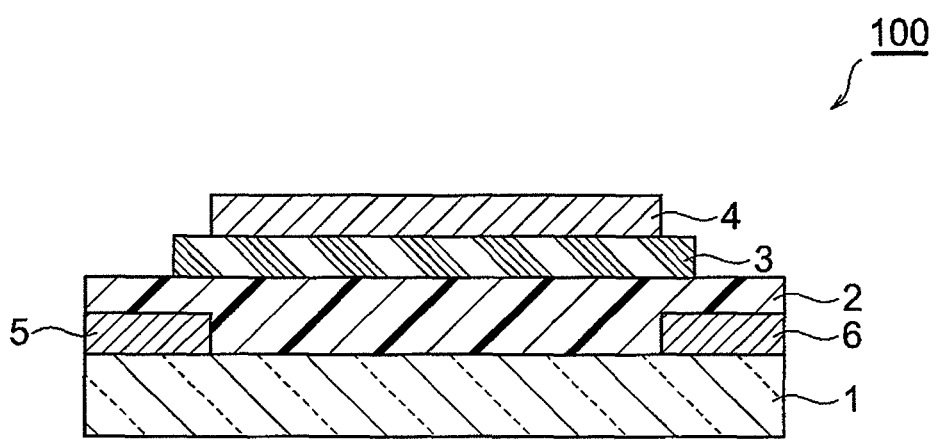
FIG. 1 is a diagram schematically illustrating the cross-sectional structure of an organic thin film transistor according to a first example.

1 ... Substrate, 2 ... Active Layer, 3 ... Insulating Layer, 4 ... Gate Electrode, 5 ... Source Electrode, 6 ... Drain Electrode, 10 ... Substrate, 12 ... Active Layer, 17a ... First Electrode, 17b ... Second Electrode, 20 ... Substrate, 22 ... Active Layer, 27a ... First Electrode, 27b ... Second Electrode, 28 ... Charge Transport Layer, 100, 110, 120, 130 ... Organic Thin Film Transistors, 200 ... Solar Cell, 300, 310, 320 ... Light Sensors

BEST MODES FOR CARRYING OUT THE INVENTION

Preferred embodiments of the present invention will now be described in more detail with reference as necessary to the drawings. In the description of the drawings, identical elements are denoted with the same reference numerals, and thus repetitive descriptions are omitted.

[Fused Ring Compound]

First, a fused ring compound according to a preferred embodiment will be described. The fused ring compound of the present embodiment is a compound represented by general formula (1). In the compound represented by general formula (1), the groups represented by $R^{11}$ or $R^{12}$ are a hydrogen atom, an alkyl group, an alkoxy group, an alkylthio group, an alkylamino group, an alkoxycarbonyl group, an optionally substituted aryl group, an optionally substituted heterocyclic group, or a cyano group. At least one of $R^{11}$ and $R^{12}$ is not a hydrogen atom, and it is preferred that both of these are not hydrogen atoms. Examples of the alkyl group include linear, branched, and cyclic alkyl groups. Further, the hydrogen atoms on the above-described functional groups may be partially or wholly substituted with a halogen atom (especially a fluorine atom).

Here, an alkyl group having 1 to 20 carbon atoms (abbreviated as "C1 to 20"; hereinafter the same) is preferred as the alkyl group. Examples of such an alkyl group include a methyl group, an ethyl group, an n-propyl group, an iso-propyl group, an n-butyl group, an iso-butyl group, a tert-butyl group, a pentyl group, a hexyl group, a heptyl group, an octyl group, a nonyl group, a decyl group, a lauryl group, a cyclopropyl group, a cyclopentyl group, a cyclohexyl group, a cycloheptyl group, a cyclooctyl group, a cyclononyl group, a cyclododecyl group and the like. Among these, a C1 to 10 alkyl group is preferred. For example, a pentyl group, a hexyl group, an octyl group, a decyl group, or a cyclohexyl group is preferred.

Further, for the alkoxy group, alkylthio group, alkylamino group, or alkoxycarbonyl group, the alkyl group on such groups is preferably a C1 to 20 alkyl group. Examples of such a C1 to 20 alkyl group include the same examples as described above.

A C6 to 60 aryl group is preferred as the optionally substituted aryl group. Examples thereof include a phenyl group, a phenyl group having a C1 to 12 alkoxy group, a phenyl group having a C1 to 12 alkyl group, a 1-naphthyl group, a 2-naphthyl group and the like. Among these, a C6 to 20 aryl group is preferred, and a phenyl group having a C1 to 12 alkoxy group or a phenyl group having a C1 to 12 alkyl group is more preferred.

A C4 to 60 heterocyclic group is preferred as the optionally substituted heterocyclic group. Examples thereof include a thienyl group, a thienyl group having a C1 to 12 alkyl group, a pyrrolyl group, a furyl group, a pyridyl group, a pyridyl group having a C1 to 12 alkyl group and the like. Among these, a C4 to 20 heterocyclic group is preferred, and a thienyl group, a thienyl group having a C1 to 12 alkyl group, a pyridyl group, or a pyridyl group having a C1 to 12 alkyl group is more preferred. Here, a "heterocyclic group" is defined as a group in which at least one of the atoms constituting the ring in an organic group having a ring structure is a hetero atom.

In the fused ring compound, $R^{11}$ and $R^{12}$ are preferably each independently an alkyl group having 1 to 20 carbon atoms or an optionally substituted aryl group having 6 to 60 carbon atoms, more preferably an alkyl group having 1 to 10 carbon atoms or an optionally substituted aryl group having 6 to 20 carbon atoms, and especially preferably an alkyl group having 1 to 10 carbon atoms.

$R^{13}$ and $R^{14}$ are each independently a monovalent group, and n and m each independently denote an integer of 0 to 2. However, when n or m is 2, each $R^{13}$ or $R^{14}$ may be the same group or a different group. Examples of $R^{13}$ and $R^{14}$ include an alkyl group, an alkoxy group, a fluoroalkyl group, a fluoroalkoxy group, an aryl group, an arylamino group or a heterocycle group. Among these, an alkyl group, an alkoxy group, a fluoroalkyl group, a fluoroalkoxy group, an aryl group, or an arylamino group is preferred, and an alkyl group or an aryl group is more preferred. Further, it is preferred that $R^{13}$ and $R^{14}$ are appropriately changed according to the carrier which is to be transported by the organic thin film including the fused ring compound. For example, in the case of increasing the hole transport properties of the organic thin film, an electron donating group such as an arylamino group is preferred, while from the perspective of increasing the electron transport properties, an electron withdrawing group such as a fluoroalkyl group or a fluoroalkoxy group is preferred.

Further, examples of a monovalent group represented by $R^{13}$ and $R^{14}$ include a polymerizable functional group. Especially, if at least one of $R^{13}$ and $R^{14}$ is a polymerizable functional group, the fused ring compound represented by general formula (1) is suitable as a raw material for the below-described polymer. In cases where the organic thin film is formed only from the fused ring compound, it is preferred that $R^{13}$ and $R^{14}$ are a group that is described above other than a polymerizable functional group.

Here, the "polymerizable functional group" is a group which can cause a polymerization reaction with another polymerizable functional group to occur. For example groups which react with and form a bond to another polymerizable functional group by undergoing a Wittig reaction, a Heck reaction, a Horner-Wadsworth-Emmons reaction, a Knoevenagel reaction, a Suzuki coupling reaction, a Grinard reaction, a Stille reaction, or a polymerization reaction using a Ni(0) catalyst and the like. Examples of the polymerizable functional group include a halogen atom, an alkylsulfonate group, an arylsulfonate group, an arylalkylsulfonate group, an alkylstannyl group, an arylstannyl group, an arylalkylstannyl group, a borate group (—B(OR)$_2$), a sulfonium methyl group, a phosphonium methyl group, a phosphonate methyl group, a monohalogenated methyl group, a boric acid group (—B(OH)$_2$), a formyl group, a vinyl group and the like. Among these, a halogen atom, an alkylstannyl group, or a borate group is preferred. Further, in these examples, R is an alkyl group or an aryl group, and 2 Rs may be joined to form a ring.

$Y^{11}$ and $Y^{12}$ are each independently a divalent group represented by general formula (2a), (2b), (2c), (2d), (2e), (2f), (2g), or (2h) (hereinafter referred to as "(2a) to (2h)"). $R^{21}$ and $R^{22}$ in these divalent groups are each independently a hydrogen atom or a monovalent group. Examples of this monovalent group include, in addition to the same groups as described above for $R^{11}$ or $R^{12}$, a halogen atom. Here, while the group represented by (2h) has an asymmetric structure, the direction that the bonding chain bonds to is not especially limited.

Among these, a divalent group represented by (2a), (2b), (2c), or (2h) is preferred for $Y^{11}$ and $Y^{12}$, and a divalent group represented by (2a), (2b), or (2c) is more preferred. If $Y^{11}$ and $Y^{12}$ are a divalent group represented by (2a), (2b), or (2c), the ring structures (two five-member rings fused to the benzene ring) including these are respectively a thiophene ring, a furan ring, or a pyrrole ring. Especially, if $Y^{11}$ and $Y^{12}$ are a divalent group represented by (2a) (specifically, if the ring structures are a thiophene ring), good charge transport properties can be obtained, and thus this is preferred.

[Polymer]

Next, the polymer according to a preferred embodiment will be described. The polymer of the present embodiment includes a monomer unit represented by general formula (3). In the monomer unit represented by general formula (3), $R^{31}$, $R^{32}$, $R^{33}$, $R^{34}$, $Y^{31}$, and $Y^{32}$ are preferably respectively the same groups as the above-described $R^{11}$, $R^{12}$, $R^{13}$, $R^{14}$, $Y^{11}$, and $Y^{12}$. However, for $R^{33}$ and $R^{34}$, groups other than the above-described polymerizable functional groups are preferred. Further, in the present embodiment, the term "polymer" refers to a substance having two or more monomer units, and includes both substances which are usually classified as oligomers and polymers.

The polymer of the present embodiment may be formed only from the monomer unit represented by general formula (3), or may further include other monomer units. Here, although a plurality of monomer units of general formula (3) are included in the polymer, the plurality of monomer units of general formula (3) may each have the same structure, or may have a different structure. However, from the perspective of easily obtaining the polymer, it is preferred that the plurality of monomer units of general formula (3) each have the same structure.

The polymer preferably further has, in addition to the monomer units of general formula (3), a monomer unit of general formula (5). By thus having a monomer unit of general formula (5), the charge transport properties from the polymer are increased, and solubility in a solvent, mechanical strength, heat resistance and the like are also improved.

The group represented by $Ar^5$ in the monomer unit of general formula (5) is an optionally substituted aromatic hydrocarbon group or an optionally substituted heterocyclic group. Such an aromatic hydrocarbon group or heterocyclic group is a group having a structure in which two substitution sites in the aromatic hydrocarbon or heterocycle are involved in the bonding in the polymer, and is a group formed from the atom group which remains after 2 hydrogen atoms have been removed from the aromatic hydrocarbon group or heterocyclic group.

The aromatic hydrocarbon group preferably is a divalent group formed preferably from a C6 to 60, and more preferably from a C6 to 20 aromatic ring (a monocycle or a fused ring). Examples of a fused ring include naphthalene, anthracene, pyrene, perylene, and fluorene. Among these, as the aromatic ring constituting this aromatic hydrocarbon group, a benzene ring or fluorene are preferred. Further, as described above, the aromatic hydrocarbon group may have a further substituent. Examples of such a substituent include a halogen atom, a saturated or unsaturated hydrocarbon group, an aryl group, an alkoxy group, an aryloxy group, a heterocyclic group, an amino group, a nitro group, or a cyano group.

Further, the heterocyclic group preferably is a divalent group formed preferably from a C4 to 60, and more preferably from a C4 to 20 heterocycle. This heterocyclic group may have a further substituent. Examples of such a substituent include the same substituents as described above for the aromatic hydrocarbon group.

In the monomer unit of general formula (5), the group represented by $Ar^5$ is preferably a group represented by general formula (6). The groups represented by $Y^6$ in general formula (6) are preferably the same as those of $Y^{11}$ or $Y^{12}$ in general formula (1). Especially preferred as $Y^6$ in the group represented by general formula (6) is a group represented by general formula (7a).

If the polymer includes both a monomer unit represented by general formula (3) and a monomer unit represented by general formula (5), a preferred ratio of these in the polymer is, based on 100 moles of monomer unit represented by general formula (3), preferably 10 to 1000 moles, more preferably 25 to 400 moles, and even more preferably 50 to 200 moles of the monomer unit represented by general formula (5).

As described above, the polymer of the present embodiment preferably includes both a monomer unit represented by general formula (3) and a monomer unit represented by general formula (5). In the polymer, the monomer units may be copolymerized randomly, or may be block copolymerized. Examples of such a polymer include polymers which have a structure represented by the following general formula (10a), (10b), or (10c). In general formula (10c), the two $Ar^5$ may each be the same or different.

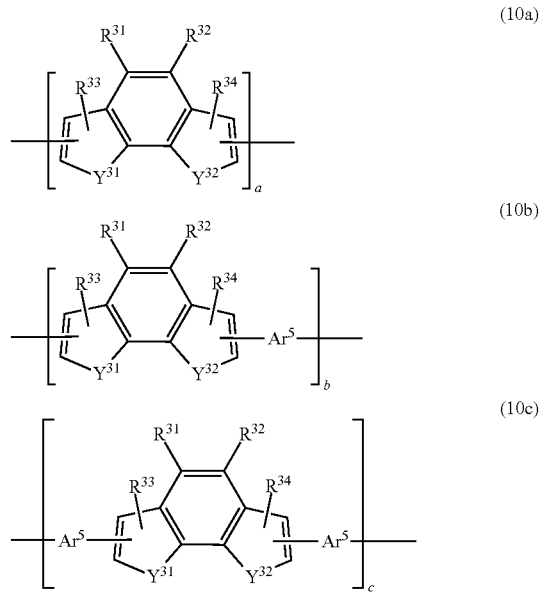

In the formula, $R^{31}$ to $R^{34}$, $Y^{31}$, $Y^{32}$, and $Ar^5$ all have the same meaning as described above. Further, a is preferably an integer of 2 to 500, and more preferably of 3 to 20. Still further, b is preferably an integer of 1 to 500, and more preferably of 2 to 20. Still further, c is preferably an integer of 1 to 500, and more preferably of 1 to 10. Especially preferred as such polymers are polymers in which $Y^{31}$ and $Y^{32}$ are both sulfide groups, $R^{31}$ and $R^{32}$ are each independently an alkyl group or an aryl group preferably an alkyl group), and $R^{33}$ and $R^{34}$ are hydrogen atoms.

The end groups of the polymer are not especially limited, and examples thereof include an electron donating group or an electron withdrawing group such as a hydrogen atom, an alkyl group, an alkoxy group, a fluoroalkyl group, a fluoroalkoxy group, an aryl group, a heterocyclic group and the like. From the perspective of increasing the charge transport properties of the polymer, the end group is preferably an electron withdrawing group such as a fluoroalkyl group or a fluoroalkoxy group. Further, the end group may also have a main chain conjugated structure or structure which can be conjugated. Examples thereof include an aryl group or a heterocyclic group having an unsaturated bond on a bonding site with the main chain.

Further, as is described below, in the case of using a fused ring compound having a polymerizable functional group as the group represented by $R^{13}$ and $R^{14}$ in general formula (1) for the raw material monomer used in the production of the polymer, the polymerizable functional group remains on the ends after polymerization. However, there is a risk that an end which is formed from such a polymerizable functional group may reduce durability and the like when an organic thin film is produced. Therefore, in the polymer, it is preferred that a polymerizable functional group is protected by a stable group.

More specifically, the polymer according to the present embodiment is preferably a polymer represented by the following general formulae (11a) to (11g).

(11a)
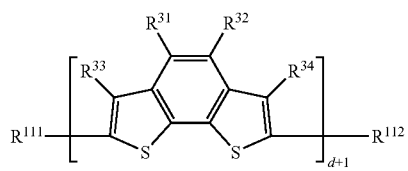

(11b)
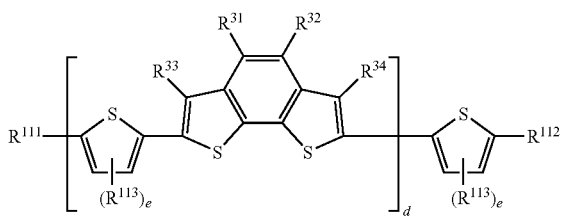

(11c)
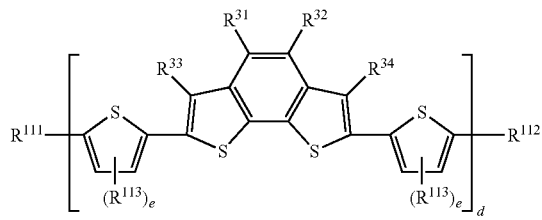

(11d)
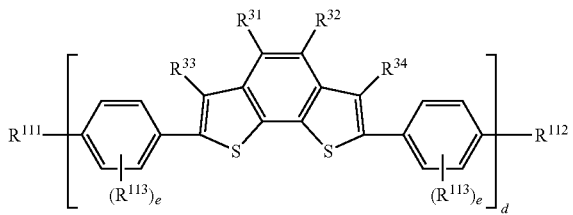

(11e)
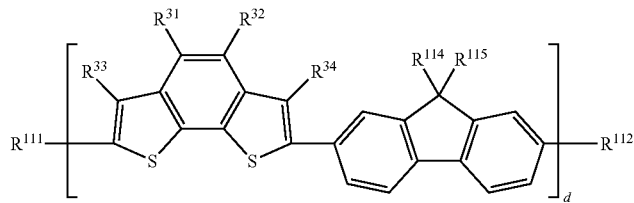

(11f)
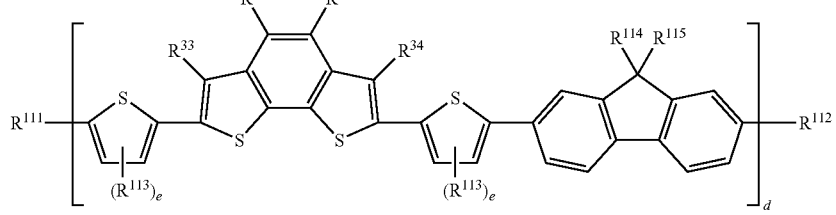

(11g)
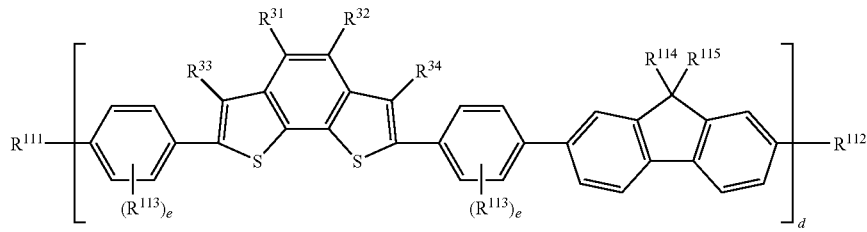

In the formulae, $R^{31}$ to $R^{34}$ have the same meaning as described above. $R^{111}$ and $R^{112}$ are each independently the above-described end groups. $R^{113}$ to $R^{115}$ each independently represent a hydrogen atom or a monovalent group. Examples of this monovalent group include the same groups which were described for $R^{13}$ and $R^{14}$ in general formula (1). Among those, an alkyl group or an alkoxy group is preferred, and an alkyl group is more preferred. Further, in the formula, d denotes an integer of 1 to 500, and e is an integer of 0 to the substitutable number for $R^{113}$. However, if a plurality of $R^{113}$ are present, these groups may be the same or different. Here, the value of d is preferably appropriately selected according to the formation method of the organic thin film in which the polymer is used. For example, when forming the organic thin film by a vapor phase growth method, such as vacuum deposition, the polymer is preferably an oligomer in which d is preferably 1 to 10, more preferably 2 to 10, and even more preferably 2 to 5. Further, when forming the organic thin film by a method of coating a solution in which the polymer was dissolved in an organic solvent, for the polymer, d is preferably 3 to 500, more preferably 6 to 300, and even more preferably 20 to 200. Still further, when forming the film by coating, from the perspective of improving the uniformity of the film, the number average molecular weight of the polymer is preferably $1 \times 10^3$ to $1 \times 10^8$, and more preferably $1 \times 10^4$ to $1 \times 10^6$.

Although the polymer has a structure in which a plurality of the structural units inside the brackets of the above-described respective general formulae are repeated, each of the plurality of structural units may have the same structure or a different structure. Specifically, the functional groups such as $R^{113}$ to $R^{115}$ in the structural units may be the same or different for each repeating unit. However, from the perspective of easily producing the polymer, it is preferred that all of the structural units have the same structure.

[Fused Ring Compound Production Method]

Next, a preferred method of producing a fused ring compound having the above-described structure will be described. The fused ring compound can be obtained by reacting a compound represented by general formula (8a) and a compound represented by general formula (8b) in the presence of a base and a metal complex catalyst. In this production method, a reaction occurs between the groups represented by $X^{81}$ and $X^{82}$ in the compound of general formula (8a) and the triple bond in the compound of general formula (8b). As a result, the two 5-membered rings in the compound of general formula (8a) are crosslinked, whereby a 6-membered ring structure is formed therebetween. It is preferred that this reaction is carried out under an inert gas atmosphere such as nitrogen or argon.

In the compound of formula (8a), for $R^{83}$, $R^{84}$, $Y^{81}$, and $Y^{82}$, the same respective groups as the groups represented by $R^{13}$, $R^{14}$, $Y^{11}$, and $Y^{12}$ in general formula (1) may be employed. Further, $X^{81}$ and $X^{82}$ are each independently a hydrogen atom or a halogen atom, and it is preferred that both of these are a halogen atom. It is preferred that at least one of $X^{81}$ and $X^{82}$ is an iodine atom, and it is more preferred that both of these are an iodine atom. If $X^{81}$ and $X^{82}$ are an iodine atom, the above-described reaction tends to occur very easily. Further, for $R^{81}$ and $R^{82}$ in the compound of general formula (8b), the same respective groups as for $R^{11}$ and $R^{12}$ in general formula (1) may be employed.

Examples of the metal complex catalyst in the above-described reaction include a palladium complex, a nickel complex, a platinum complex, a ruthenium complex, a rhodium complex, or an iridium complex. Among these, a palladium complex or a nickel complex is preferred, and a palladium complex is more preferred. The palladium complex is not especially restricted, although a complex which can promote a coupling reaction of an aromatic halide is preferred. Examples of such a palladium complex include a divalent palladium complex, a palladium complex compound which has an electron donating ligand and the like.

Examples of the divalent palladium complex include palladium acetate, palladium chloride, sodium palladate, potassium palladate and the like. Palladium acetate is preferred. Examples of the palladium complex compound which has an electron donating ligand include tetrakis(triphenylphosphine)palladium, dichlorobis(triphenylphosphine)palladium, tris(dibenzylideneacetone)dipalladium and the like. Tetrakis(triphenylphosphine)palladium is preferred.

As the metal complex catalyst, a single kind of those described above may be employed, or a combination of a plurality of kinds thereof may be employed. It is preferred to use 0.01 to 50 mol %, more preferred to use 1.0 to 20 mol %, and even more preferred to use 3 to 15 mol %, of the metal complex catalyst based on the raw material compound represented by general formula (8a).

Further, either an inorganic base or an organic base may be used as the base, although an organic base is more preferred. Examples of inorganic bases include the hydroxide of alkaline metals or alkaline-earth metals, carbonates, ammonium salts, acetates and the like. Examples of organic bases include trialkylamines, dialkylarylamines and alkyldiarylamines which contain a C1 to 20 alkyl group, amines such as triarylamine, pyridine and the like.

Specific examples of the organic base include trimethylamine, triethylamine, diisopropylethylamine, tri-n-propylamine, tributylamine, dicyclohexylmethylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine and the like.

Amines are especially preferred as the organic base. By using an amine as the organic base, the formation of byproducts during the reaction can be suppressed, thereby allowing the target fused ring compound to be obtained in a high yield. Among amines, an alkylamine, and especially trialkylamine, are preferred. Preferred as such an alkylamine is an amine in which the carbon adjacent to the nitrogen atom has one or more hydrogen atoms, specifically, an amine having a structure represented by N—CHx (wherein X is 1 to 3). More preferred is an amine in which the carbon adjacent to the nitrogen atom has two or more hydrogen atoms, specifically, an amine having a structure represented by N—CHx (wherein X is 2 or 3).

The above-described reaction can also be carried out in a solvent. The solvent used in the reaction is preferably inert in a reaction carried out using a metal complex catalyst. Examples include toluene, dimethylformamide (DMF), N-methyl-2-pyrrolidone (NMP), tetrahydrofuran (THF), dioxane, isopropyl alcohol, acetonitrile, pinacolone and the like. Among these, toluene, NMP, or dioxane is preferred. Although the amount of solvent used is not especially limited, a preferred amount can be, for example, 1 to 100 times, and more preferably 2 to 30 times, the weight of the raw material compound represented by general formula (8a).

The reaction time is not especially limited. The time may be set so that the reaction finishes at the point where either one of the compound of general formula (8a) or the compound of general formula (8b) runs out. The time from reaction start to finish is about 0.5 to 200 hours. Further, the reaction temperature may be appropriately set in the range of −50 to 300° C., and is preferably set at about 50 to 150° C.

To obtain a high-purity organic thin film, after the above-described reaction, the obtained fused ring compound is preferably purified by distillation, sublimation, recrystallization and the like.

While a fused ring compound can be suitably obtained by the above-described production method, in such a production method, the reaction expressed by the following reaction equation occurs, whereby the fused ring compound represented by the following general formula (8c) is obtained. It is noted that other reactions may also occur. Here, the following reaction equation is an example of a case in which iodine atoms were used for $X^{81}$ and $X^{82}$.

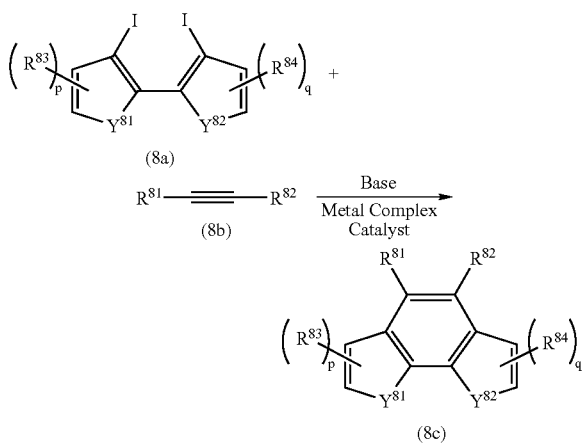

(8a)

(8b)

(8c)

[Polymer Production Method]

Next, a preferred method for producing a polymer compound having the above-described structure will be described. In the following description, a method is described in which a polymer is produced having both a monomer unit represented by general formula (3) and a monomer unit represented by general formula (5).

The polymer can be obtained by carrying out polymerization by reacting a monomer represented by the following general formula (13a) and a monomer represented by the following general formula (13b).

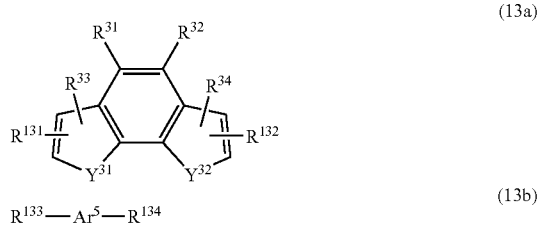

(13a)

(13b)

In the formula, $R^3$ to $R^{34}$, $Y^{31}$, and $Y^{32}$ all have the same meaning as described above. Further, $R^{131}$ to $R^{134}$ are each independently a polymerizable functional group. Examples of such a polymerizable functional group include the same groups as described as the polymerizable functional group for $R^{13}$ and $R^{14}$ in general formula (1).

To obtain the polymer, a reaction in which a bond is formed between a compound represented by general formula (13a) and a compound represented by general formula (13b), or between compounds represented by general formula (13a), or between compounds represented by general formula (13b), is repeatedly carried out. Examples of reactions in which a bond is formed between the above-described compounds include a Wittig reaction, a Heck reaction, a Horner-Wadsworth-Emmons reaction, a Knoevenagel reaction, a Suzuki coupling reaction, a Grinard reaction, a Stille reaction, and a polymerization reaction using a Ni(0) catalyst and the like. In addition, a reaction in which an intermediate compound having a suitable leaving group is decomposed may also be employed. An example thereof includes a method in which poly(p-phenylenevinylene) is synthesized from an intermediate compound having a sulfonium group. It is preferred to appropriately select the above-described $R^{131}$ to $R^{134}$ polymerizable functional groups according to the target reaction. Further, the polymer may also be formed other than by a reaction by polymerizable functional groups. An example thereof is a method in which fused ring compounds in which n and m in general formula (1) are 0 are repeatedly joined by an oxidative polymerization reaction using $FeCl_3$ or a polymerization reaction by electrochemical oxidation.

The reaction for obtaining the polymer is, among those described above, preferably a Suzuki coupling reaction, a Grinard reaction, a Stille reaction, or a polymerization reaction using a Ni(0) catalyst, since in such reactions production control is easy and the preparation of the raw material is relatively easy, yet the reaction procedures are simple. Further, the oxidative polymerization reaction using $FeCl_3$ is also preferable, because the preparation of the raw material is relatively easy, yet the reaction procedures are simple.

Specific examples of preferred polymerizable functional group combinations in these reactions include: for the Suzuki coupling reaction, a combination of a boric acid group or borate group and a halogen; for the Grinard reaction, a combination of a halomagnesium carbanion and a halogen; for the Stille reaction, a combination of an alkylstannyl group and a halogen; and for the polymerization reaction using a Ni(0) catalyst, a combination of halogens.

To suppress side reactions, it is preferred that the reaction for obtaining the polymer is carried out under an inert gas atmosphere. Further, from the perspective of obtaining a high-purity organic thin film from the polymer, the raw material monomers are preferably purified by various methods, such as distillation, sublimation, and recrystallization. In addition, after the reaction, the polymer, which is the target product, is extracted with an organic solvent and then isolated from the resultant extract by removing the solvent by distillation. However, it is preferred to further purify this polymer by a means such as chromatography or recrystallization.

Further, each of the above-described reactions can be carried out in a solution in which the raw material monomers were dissolved in a solvent. In such case, it is preferred to optionally add and dissolve a base, a catalyst and the like, and carry out the reactions at a temperature at or below the boiling point of the solvent.

Although the solvent depends on the reaction which is to be carried out, examples of preferred solvents include saturated hydrocarbons such as pentane, hexane, heptane, octane, and cyclohexane, aromatic hydrocarbons such as benzene, toluene, ethylbenzene, and xylene, halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane, halogenated aromatic hydrocarbons such as chlorobenzene, dichlorobenzene, and trichlorobenzene, alcohols such as methanol, ethanol, propanol, isopropyl alcohol, butanol and t-butyl alcohol, carboxylic acids such as formic acid, acetic acid, and propionic acid, ethers such as dimethyl ether, diethyl ether, methyl-t-butyl ether, tetrahydrofuran, tetrahydropyran, and dioxane, inorganic acids such as hydrochloric acid, bromic acid, hydrofluoric acid, sulfuric acid, and nitric acid and the like. A plurality of these may optionally be combined. From the perspective of suppressing side reactions, it is preferred to use a solvent which was thoroughly subjected to a deoxidation treatment.

[Organic Thin Film]

Next, an organic thin film according to a preferred embodiment will be described. The organic thin film includes the fused ring compound and/or polymer according to the above-described embodiments, and has a structure having a film form. The organic thin film may include only one of the fused ring compound and the polymer, or may include both of these. Further, in the organic thin film, two kinds or more of the fused ring compound or polymer may be included.

Further, the organic thin film may be formed from only the fused ring compound or polymer, or may further include other components. Although the preferred thickness of such an organic thin film depends on the device in which the organic thin film is applied, the thickness is usually in the range of 1 nm to 100 μm, preferably 2 nm to 1000 nm, more preferably 5 nm to 500 nm, and even more preferably 20 nm to 200 nm.

To obtain excellent charge (hole or electron) transport properties, the organic thin film may further include a compound having hole transport properties or electron transport properties. Examples of a compound having hole transport properties include a pyrazoline derivative, an arylamine derivative, a stilbene derivative, a triphenyldiamine derivative, an oligothiophene or its derivative, a polyvinylcarbazole or its derivative, a polysilane or its derivative, a polysiloxane derivative having an aromatic amine in a side chain or main chain, a polyaniline or its derivative, a polythiophene or its derivative, a polypyrrole or its derivative, a polyphenylene vinylene or its derivative, a polythienylene vinylene or its derivative or the like.

Further, examples of a compound having electron transport properties include an oxadiazole derivative, anthraquinodimethane or its derivative, benzoquinone or its derivative, naphthoquinone or its derivative, anthraquinone or its derivative, tetracyanoanthraquinodimethane or its derivative, a fluorenone derivative, diphenyldicyanoethylene or its derivative, a diphenoquinone derivative, a metal complex of 8-hydroxyquinoline or its derivative, a polyquinoline or its derivative, a polyquinoxaline or its derivative, a polyfluorene or its derivative, and a $C_{60}$ etc. fullerene or its derivative and the like.

The organic thin film may further include other components in order to improve its properties. Examples of such other components include a charge generation material and the like. By including a charge generation material in the organic thin film, the thin film generates a charge from the absorption of light, which is suited for applications such as a light sensor which require charge generation from the absorption of light.

Examples of the charge generation material include an azo compound or its derivative, a diazo compound or its derivative, a non-metal-phthalocyanine compound or its derivative, a metal-phthalocyanine compound or its derivative, a perylene compound or its derivative, a polycyclic quinone compound or its derivative, a squarylium compound or its derivative, an azulenium compound or its derivative, a thiapyrylium compound or its derivative, and a $C_{60}$ etc. fullerene or its derivative and the like.

Further, the organic thin film may further contain a sensitizer for increasing the sensitivity of the charge generation function by the above-described charge generation material, a stabilizing agent for stabilizing the thin film, a UV absorber for absorbing UV light and the like.

Further, from the perspective of increasing the mechanical strength, the organic thin film may further contain a polymeric compound other than the fused ring compound or polymer as a polymeric binder. It is preferred that such polymeric binder does not excessively decrease the charge transport properties, and that it does not excessively absorb visible light.

Examples of the polymeric binder include poly(N-vinylcarbazole), polyaniline or its derivative, polythiophene or its derivative, poly(p-phenylenevinylene) or its derivative, poly (2,5-thienylenevinylene) or its derivative, polycarbonate, polyacrylate, polymethylacrylate, polymethyl methacrylate, polystyrene, polyvinyl chloride, polysiloxane and the like.

The above-described organic thin film can be produced, for example, by the following method.

Specifically, the organic thin film can be formed by coating a solution, in which the fused ring compound and/or polymer, and optionally the above-described other components were dissolved in a solvent, on a certain substrate, and then removing the solvent by volatilization or the like.

It is preferred that the solvent can dissolve or uniformly disperse the fused ring compound or polymer and the other components. Examples of the solvent include aromatic hydrocarbon solvents such as toluene, xylene, mesitylene, tetralin, decalin and n-butylbenzene, halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane, halogenated aromatic hydrocarbon solvents such as chlorobenzene, dichlorobenzene, and trichlorobenzene, and ether solvents such as tetrahydrofuran and tetrahydropyran and the like. It preferred to dissolve 0.1 mass % or more of the fused ring compound or polymer in the solvent.

Examples of the method for coating the solution include spin coating, casting, micro gravure coating, gravure coating, bar coating, roll coating, wire bar coating, dip coating, spray coating, screen printing, flexo printing, offset printing, inkjet printing, dispenser printing and the like. Among these, spin coating, flexo printing, inkjet printing, or dispenser printing is preferred.

While the organic thin film can be obtained by a method such as that described above, the method for producing the organic thin film is not necessarily limited thereto. For example, in the case of using for the raw materials low molecular weight materials for the fused ring compound, oligomer and the like, a vapor phase growth method, such as vacuum deposition, may be employed.

The organic thin film may be further subjected to a step for orienting the fused ring compounds or polymers in the organic thin film according to how the organic thin film is to be used. By carrying out this orientation, the fused ring compound or polymers in the organic thin film (main chain or side chains) are aligned in a fixed direction, whereby the charge transport properties of the organic thin film are further increased.

As an organic thin film orientation method, a method which is typically used in the orientation of liquid crystals and the like may be employed. Specifically, a rubbing method, a photo-orientation method, a shearing method (shearing stress application method) and the like are preferred, as such methods are simple and useful. A rubbing method or a shearing method are more preferred.

[Organic Thin Film Device]

Since the organic thin film of the above-described embodiment includes the fused ring compound and/or polymer of the above-described embodiments, it has excellent charge (electron or hole) transport properties. Therefore, this organic thin film can efficiently transport electrons or holes which have been injected from an electrode and the like, or a charge etc. generated by light absorption. Thus, this organic thin film can be applied to various electric devices (organic thin film devices) which use an organic thin film. Examples of organic thin film devices will now be respectively described below.

(Organic Thin Film Transistor)

First, an organic thin film transistor according to a preferred embodiment will be described. The organic thin film transistor has source and drain electrodes, an active layer which acts as a current pathway between the source and drain electrodes and which is formed from an organic thin film including the fused ring compound of the above embodiments or a polymer containing such fused ring compound, a gate electrode for controlling the current passing through the current pathway, and an insulating layer arranged between the active layer and the gate electrode. Such an organic transistor is a so-called field-effect transistor, which controls the current amount flowing through the active layer by regulating the voltage applied to the gate electrode. Preferred structures of such an organic thin film transistor will now be described with reference to FIGS. 1 to 4.

FIG. 1 is a diagram schematically illustrating the cross-sectional structure of an organic thin film transistor according to a first example. As illustrated in the drawing, an organic thin film transistor 100 has a structure configured from a substrate 1, a source electrode 5 and a drain electrode 6 which are formed on this substrate 1, an active layer 2 formed on the substrate 1 so as to cover the source electrode 5 and drain electrode 6, an insulating layer 3 formed on the active layer 2, and a gate electrode 4 formed on the insulating layer 3.

The substrate 1 is not especially limited as long as its characteristics as a transistor are not easily affected. Examples thereof include a glass substrate, a plastic substrate, a flexible film substrate or the like. The active layer 2 is formed from the organic thin film according to the present invention. Such an active layer 2 can be formed by forming the organic thin film on the substrate 1 by a formation method such as that described above.

The insulating layer 3 is formed between the active layer 2 and the gate electrode 4, thereby electrically insulating these parts. Examples of the insulating layer 3 include materials composed of $SiO_x$, $SiN_x$, $Ta_2O_5$, polyimide, polyvinyl alcohol, polyvinyl phenol and the like. From the perspective of lowering the drive voltage, a material having a high dielectric constant is preferable.

The gate electrode 4 is formed from a conductive material. Examples of the conductive material include metals such as aluminum, gold, platinum, silver, copper, chromium, nickel, and titanium, conductive oxides such as ITO, conductive polymers such as mixed polymers of poly(3,4-ethylenedioxythiophene) and polystyrene sulfonic acid and the like. Further, conductive materials in which metal particles, carbon black, or graphite fine powder is dispersed in the binder can also be employed. The source electrode 5 and the drain electrode 6 are provided so that they are both in contact with the active layer 2, and are formed from the same conductive material as the gate electrode 4.

Although the organic thin film transistor 100 has a structure in which the active layer 2 and the insulating layer 3 are adhered closely together, to improve the interfacial properties between these layers, it is preferred to modify the surface of the insulating layer 3 on the side in contact with the active layer 2 by treating with a surface treatment agent such as a silane coupling agent and the like. Examples of the surface treatment agent include silylamine compounds such as long-chain alkylchlorosilanes, long-chain alkylalkoxysilanes, fluorinated alkylchlorosilanes, fluorinated alkylalkoxysilanes, hexamethyldisilazane and the like. Before carrying out the treatment with a surface treatment agent, the surface of the insulating layer 3 may be treated with ozone UV, $O_2$ plasma and the like.

Figure 2:
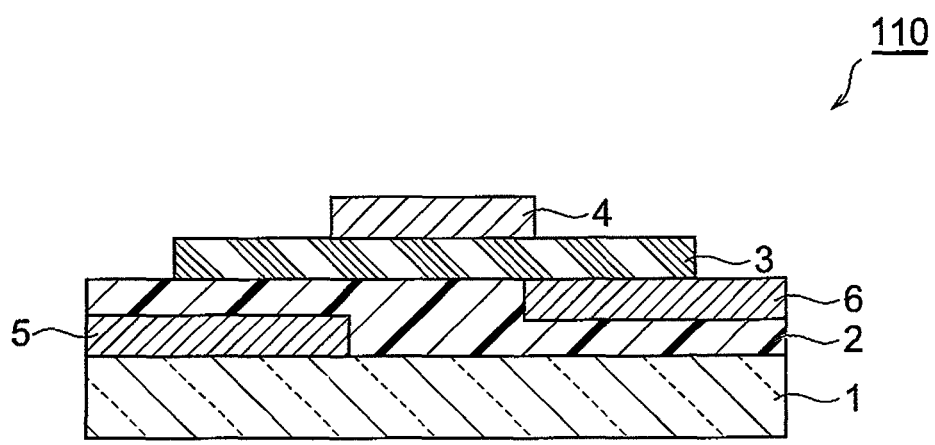
FIG. 2 is a diagram schematically illustrating the cross-sectional structure of an organic thin film transistor according to a second example.

FIG. 2 is a diagram schematically illustrating the cross-sectional structure of an organic thin film transistor according to a second example. An organic thin film transistor 110 has a substrate 1, a source electrode 5 provided on the substrate 1, an active layer 2 provided on the substrate 1 so as to cover the source electrode 5, a drain electrode 6 provided on the active layer 2, an insulating layer 3 provided on the active layer 2, and a gate electrode 4 provided on the insulating layer 3. Thus, in the organic thin film transistor 110, the source electrode 5 and the drain electrode 6 are respectively formed on different sides of the active layer 2.

Figure 3:
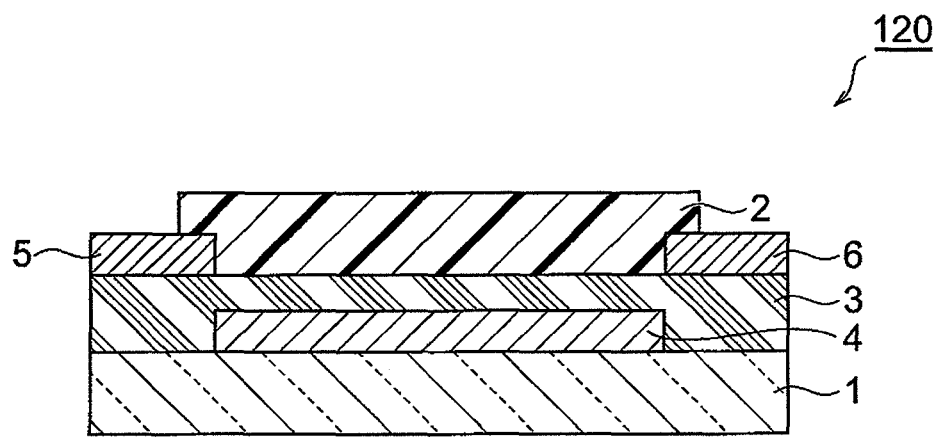
FIG. 3 is a diagram schematically illustrating the cross-sectional structure of an organic thin film transistor according to a third example.

FIG. 3 is a diagram schematically illustrating the cross-sectional structure of an organic thin film transistor according to a third example. An organic thin film transistor 120 has a substrate 1, a gate electrode 4 provided on the substrate 1, an insulating layer 3 provided on the substrate 1 so as to cover the gate electrode 4, a source electrode and a drain electrode 6 provided on the insulating layer 3, and an active layer 2 provided on the insulating layer 3 so as to be in contact with the source electrode 5 and drain electrode 6.

Figure 4:
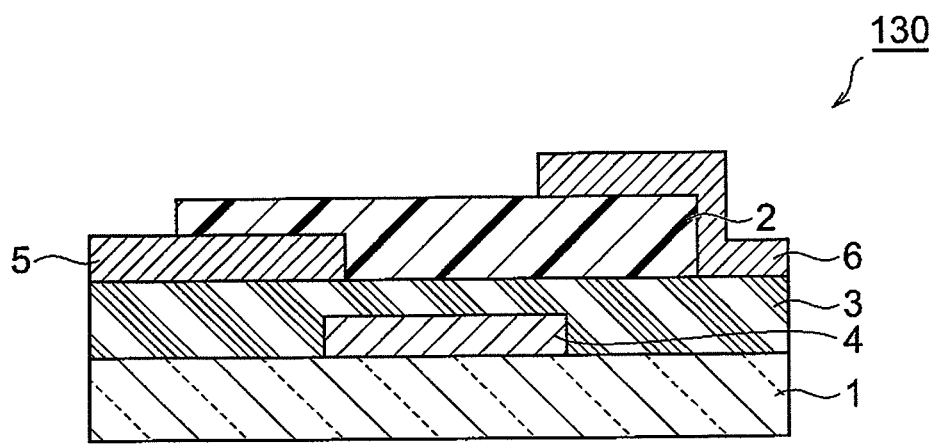
FIG. 4 is a diagram schematically illustrating the cross-sectional structure of an organic thin film transistor according to a fourth example.

FIG. 4 is a diagram schematically illustrating the cross-sectional structure of an organic thin film transistor according to a fourth example. An organic thin film transistor 130 has a substrate 1, a gate electrode 4 provided on the substrate 1, an insulating layer 3 provided on the substrate 1 so as to cover the gate electrode 4, a source electrode 5 provided on the insulating layer 3, an active layer 2 provided on the insulating layer 3 so as to cover the source electrode 5, and a drain electrode 6 which is provided on the active layer 2 and which has an edge portion which is in contact with the insulating layer 3.

In the organic thin film transistors described in the first to fourth examples, the active layer 2 acts as a current pathway (channel) between the source electrode 5 and the drain electrode 6. Further, by applying a voltage the gate electrode 4 controls the current amount passing through the current pathway (channel) in the active layer 2. Such an organic thin film transistor can be produced by a well-known method. Examples of such a production method include that described in Japanese Patent Laid-Open No. 5-110069.

The organic thin film transistor of the above-described embodiment may have a device structure (the structure including the active layer 2, insulating layer 3, gate electrode 4, source electrode 5, and drain electrode 6) which is covered by a protective film in order to improve its durability and the like. As a result, contact between the device and the air is suppressed, which enables the deterioration in the characteristics of the organic thin film transistor over time to be reduced. Further, if some other electric device, such as a display device, is formed on the organic thin film transistor, covering the structure with a protective film also allows adverse affects on the formation process of that device structure to be reduced.

Examples of such a protective film include inorganic films such as a UV curing resin, a thermosetting resin, and a $SiON_x$ film. The formation of the protective film is preferably carried out under conditions in which the device structure does not come into contact with air, such as in a dry nitrogen atmosphere, or under a vacuum. By forming under such conditions, it is much more difficult for the organic thin film transistor to deteriorate over time.

One example of a method for producing the organic thin film transistor will now be described in more detail. Specifically, first, a solution of the polymer (oligomer), which is the constituent material of the active layer 2, in dichlorobenzene is prepared. Further, a heavily-doped n-type silicon substrate which acts as both the substrate 1 and the gate electrode 4 (this will be referred to as substrate 1) is prepared. Then, the surface of this substrate is thermally oxidized to produce a 200 nm silicon oxide film for forming an insulating layer 3. The surface of this insulating layer 3 is subjected to ultrasonic cleaning with an alkali detergent, ultrapure water, and acetone, and then cleaned by ozone UV irradiation.

Next, gold is deposited on the insulating layer 3 by vacuum deposition to form a source electrode 5 and a drain electrode 6 having a channel width of 2 mm and a channel length of 20 μm. Then, the laminated body formed with the substrate 1, the insulating layer 3, the source and drain electrodes 5 and 6 is placed on a spin coater. Hexamethyldisilazane (HMDS, manufactured by Ardrich) is added dropwise onto the surface on the side on which the source and drain electrodes 5 and 6 are formed, and then the laminated body is spun at 2000 rpm to treat the surface with HMDS.

Subsequently, the above-described solution of the oligomer in dichlorobenzene is coated on the HMDS-treated surface of the laminated body by spin coating to form on this surface an active layer 2 formed from an organic thin film, thereby obtaining an organic thin film transistor. The thus-obtained organic thin film transistor has the same structure as the organic thin film transistor 120 illustrated in FIG. 3, wherein the gate electrode 4 also acts as the substrate 1.

If the transistor characteristics of an organic thin film transistor having such a structure are measured in a vacuum by varying the gate voltage and the voltage between the source and the drain, good Isd-Vg characteristics are obtained.

(Solar Cell)

Figure 5:
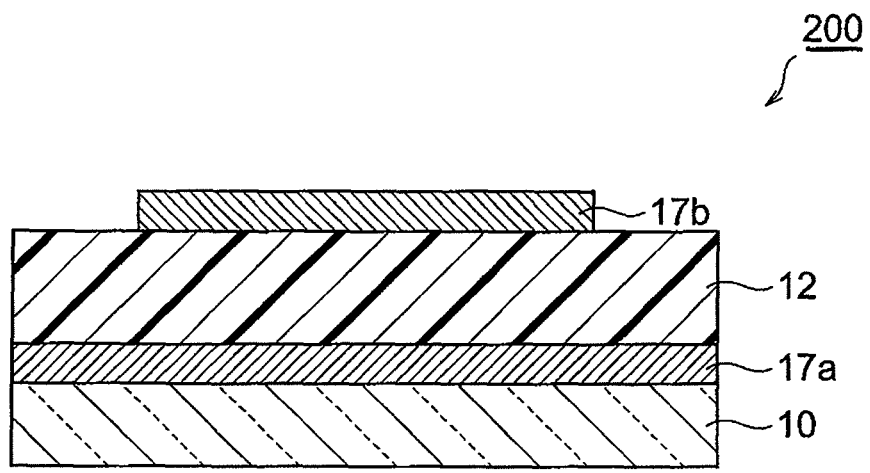
FIG. 5 is a diagram schematically illustrating the cross-sectional structure of a solar cell according to a preferred embodiment.

Next, a solar cell according to a preferred embodiment will be described. FIG. 5 is a diagram schematically illustrating the cross-sectional structure of a solar cell according to a preferred embodiment. A solar-cell 200 has a structure provided with a first electrode 17a, an active layer 12, and a second electrode 17b on a substrate 10 in that order. The substrate 10 is preferably a silicon substrate, a glass substrate, a plastic substrate and the like. Further, the active layer 12 is formed from the organic thin film according to the present invention. This active layer 12 may further include a carrier generator, a sensitizer and the like to increase sensitivity to light.

Examples of the electrode material forming the first electrode 17a or second electrode 17b include metals such as aluminum, gold, silver, copper, alkali metals, and alkali rare earth metals. A transparent or semitransparent material is employed for at least one of the first electrode 17a and second electrode 17b. To obtain a high open voltage, it is preferred to combine electrode materials so as to have a large difference in work function between the first electrode 17a and second electrode 17b.

(Light Sensor)

Figure 6:
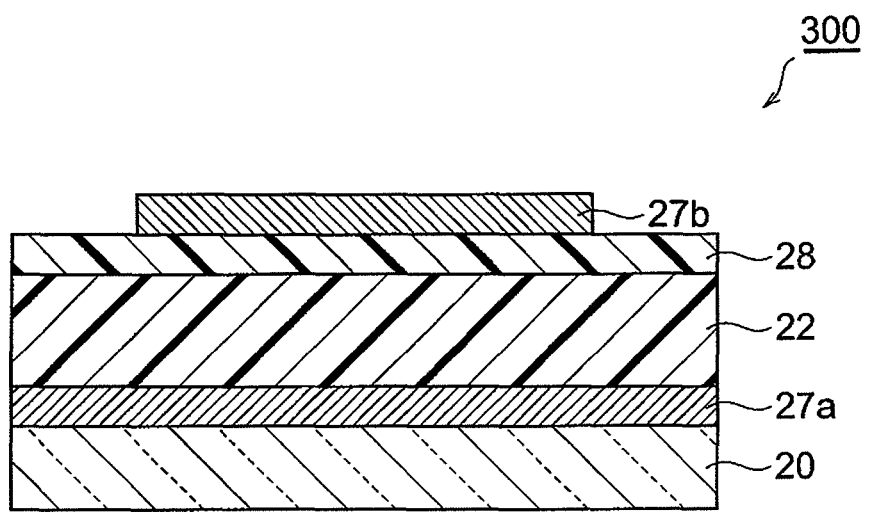
FIG. 6 is a diagram schematically illustrating the cross-sectional structure of a light sensor according to a first example.

Next a light sensor according to a preferred embodiment will be described. FIG. 6 is a diagram schematically illustrating the cross-sectional structure of a light sensor according to a first example. The light sensor 300 illustrated in FIG. 6 has a structure provided with a first electrode 27a, an active layer 22, a charge generation layer 28, and a second electrode 27b on a substrate 20 in that order. For the substrate 20, active layer 22, first electrode 27a, and second electrode 27b, the same respective structures as those of the substrate 10, active layer 12, first electrode 17a, and second electrode 17b in the solar cell may be employed.

The charge generation layer 28 is formed between at least one of the electrodes and the active layer 22. This charge generation layer 28 is a layer which absorbs lights for generating a charge. For the constituent material of the charge generation layer 28, the various charge generation materials which may be employed for the above-described organic thin film can be employed.

Figure 7:
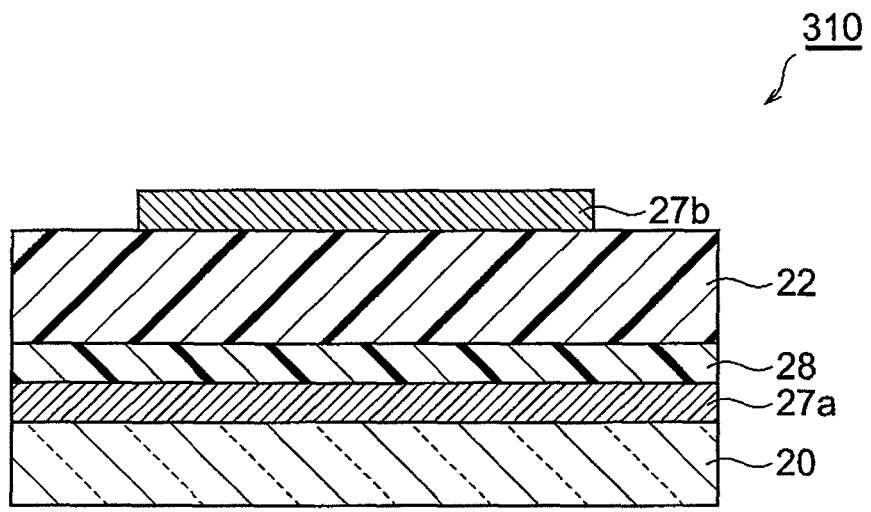
FIG. 7 is a diagram schematically illustrating the cross-sectional structure of a light sensor according to a second example.

FIG. 7 is a diagram schematically illustrating the cross-sectional structure of a light sensor according to a second example. The light sensor 310 illustrated in FIG. 7 has a structure provided with a first electrode 27a, a charge generation layer 28, an active layer 22, and a second electrode 27b on a substrate 20 in that order.

Figure 8:
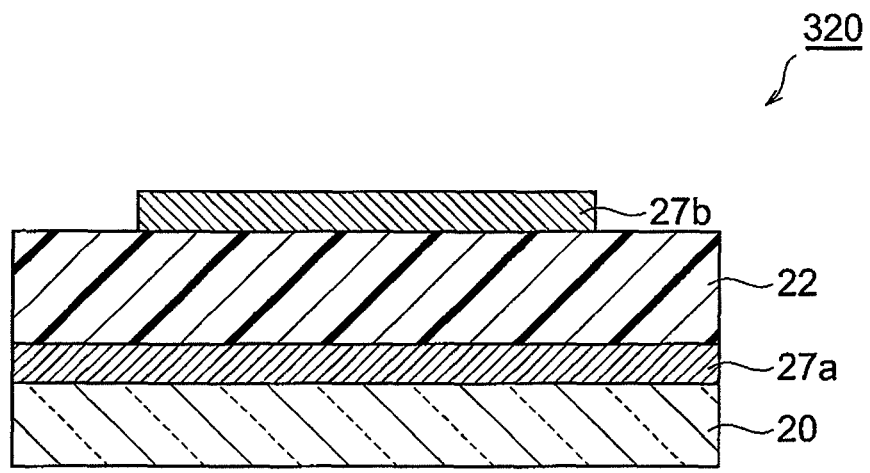
FIG. 8 is a diagram schematically illustrating the cross-sectional structure of a light sensor according to a third example.

FIG. 8 is a diagram schematically illustrating the cross-sectional structure of a light sensor according to a third example. The light sensor 320 illustrated in FIG. 8 has a structure provided with a first electrode 27a, an active layer 22, and a second electrode 27b on a substrate 20 in that order. Thus, in cases where the active layer 22 formed from an organic thin film can itself generate a sufficient charge from the incidence of light, the light sensor does not have to have a charge generation layer 28 like in the first and second examples.

While embodiments of an organic thin film device employing the organic thin film according to the present invention were described above, the organic thin film device is not limited to the above-described embodiments as long as the electric device employs an organic thin film. Examples of organic thin film devices other than those described above include organic EL devices, organic memories, photorefractive devices, spatial light modulators, imaging devices and the like.

EXAMPLES

The present invention will now be described in more detail by the following examples. However, the present invention is not limited to these examples.

(Measurement Conditions)

In the following synthesis examples and examples, various analyses and the like were carried out under the following conditions. Specifically, first, nuclear magnetic resonance (NMR) spectra were measured using a JNM-GSX-400 manufactured by JEOL Ltd. Gas chromatography mass spectrometry (GC-MS) was carried out by electron bombardment using a QP-5050 manufactured by Shimadzu Corporation. High resolution mass spectrometry (HRMS) was carried out using a JMS-DX-303 manufactured by JEOL Ltd. Gas chromatograph analysis (GC) was carried out using a GC-8A manufactured by Shimadzu Corporation mounted with a glass column (2.6 mm inner diameter, 1.5 m length) packed with silicon OV-17 manufactured by GL Sciences Inc. The silica gel used in the column chromatography separation was Wako Gel C-200 manufactured by Wako Pure Chemical Industries, Ltd.

Synthesis Example 1

Synthesis of 3,3'-diiodo-2,2'-bithiophene

First, the starting raw material 3,3'-dibromo-2,2'-bithiophene was synthesized by referring to the description in a reference document (Hong M., Wei H., J. Org. Chem., 2000, 65, 3895). Then, a halogen exchange reaction was carried out using this starting raw material to synthesize 3,3'-diiodo-2,2'-bithiophene. Specifically, first, a three-necked 300 mL flask was charged with 3,3'-dibromo-2,2'-bithiophene (2.7 g (7 mmol)), which was then dissolved in diethyl ether (70 mL). Next, the contents of the reaction vessel were purged with nitrogen and the vessel was cooled to −78° C. Then, the vessel was charged with butyllithium (in 1.5 M hexane solution, 10.3 mL (15.4 mmol)), and the resultant solution was stirred for 1 hour. Iodine (3.9 g (15.4 mmol) dissolved in diethyl ether was further charged thereto, and the resultant solution was reacted by stirring for 1 hour at room temperature.

The post-reaction solution was charged with diethyl ether (about 50 mL), and the resultant solution was then washed with a saturated aqueous sodium thiosulfate solution. Subsequently, the organic layer was dried over sodium sulfate, and then filtered over Celite. The solvent was removed from the filtrate by distillation, and then the resultant solid was recrystallized with hexane and toluene to obtain the target product 3,3'-diiodo-2,2'-bithiophene as a white solid (1.9 g, 65% yield). The melting point of the obtained white solid was measured to be 148° C. (Document value 149.5 to 151° C.; Gronowitz S., Vilks V., Arkiv Kemi, 1963, 21, 191.)
[Fused Ring Compound Production]

Example 1

Synthesis of 4,5-di(n-propyl)benzo[2,1-b:3,4-b'] dithiophene

A two-necked 20 mL flask was charged with 3,3'-diiodo-2,2'-bithiophene (84 mg (0.2 mmol)), palladium(II) acetate (4.5 mg (0.02 mmol)), 4-octyne (66 mg (0.6 mmol)), N,N-dicyclohexylmethylamine (117 mg (0.6 mmol)), and N,N-dimethylformamide (2.5 mL). The contents of the reaction vessel were purged with nitrogen, and a reaction was then carried out under stirring by heating at 100° C. Four hours later, it was confirmed by GC and GC-MS analysis that 4,5-di(n-propyl)benzo[2,1-b:3,4-b']dithiophene was roughly quantitatively (GC yield of 99% or more) formed in the reaction mixture.

Next, the obtained reaction solution was charged with diethyl ether (about 20 mL), and the resultant solution was then washed with water. Subsequently, the organic layer was dried over sodium sulfate, and then filtered over Celite. The solvent was removed from the filtrate by distillation, and then the remaining liquid was purified by silica gel column chromatography using hexane as a developing solvent to obtain the target product 4,5-di(n-propyl)benzo[2,1-b:3,4-b'] dithiophene as an oily substance (46 mg) The obtained target product $^1$H-NMR and HRMS measurement results were as follows.

$^1$H-NMR (400 MHz, CDCl$_3$, ppm): δ7.45 (d, J=5.5 Hz, 2H), 7.35 (d, J=5.5 Hz, 2H), 3.01 (m, 4H), 1.74-1.64 (m, 4H), 1.07 (t, J=7.3 Hz, 6H).

HRMS (EI): m/z 274.0847 (Value obtained by measuring with C$_{16}$H$_{18}$S$_2$ was 274.0850.)

Example 2

A reaction was carried out in the same manner as in Example 1, except that tributylamine (111 mg (0.6 mmol)) was used instead of N,N-dicyclohexylmethylamine, and the reaction time was 8 hours. After the reaction, it was confirmed from GC and GC-MS analysis that 4,5-di(n-propyl)benzo[2,1-b:3,4-b']dithiophene was roughly quantitatively (GC yield of 99% or more) formed in the reaction mixture.

Example 3

A reaction was carried out in the same manner as in Example 1, except that tributylamine (111 mg (0.6 mmol)) was used instead of N,N-dicyclohexylmethylamine, dicyclohexylmethylamine (76 mg (0.6 mmol)) was used, and the reaction time was 8 hours. After the reaction, it was confirmed from GC and GC-MS analysis that 92% of 4,5-di(n-propyl) benzo[2,1-b:3,4-b']dithiophene was formed in terms of GC yield in the reaction mixture.

Example 4

A reaction was carried out in the same manner as in Example 1, except that diisopropylethylamine (78 mg (0.6 mmol)) was used instead of N,N-dicyclohexylmethylamine, and the reaction time was 6 hours. After the reaction, it was conformed from GC and GC-MS analysis that 88% of 4,5-di(n-propyl)benzo[2,1-b:3,4-b']dithiophene was formed in terms of GC yield in the reaction mixture.

Example 5

Synthesis of 4,5-di(n-pentyl)benzo[2,1-b:3,4-b'] dithiophene

A two-necked 20 mL flask was charged with 3,3'-diiodo-2,2'-bithiophene (84 mg, 0.2 mmol), palladium(II) acetate (2.2 mg, 0.01 mmol), 6-dodecene (40 mg, 0.24 mmol), N,N-dicyclohexylmethylamine (94 mg, 0.48 mmol), and N,N-dimethylformamide (2.5 mL). The contents of the reaction vessel were purged with nitrogen, and a reaction was then carried out under stirring by heating at 130° C.

After 3 hours, the reaction solution was charged with diethyl ether (about 20 mL), and the resultant solution was then washed with water. Subsequently, the organic layer was dried over sodium sulfate, and filtered over Celite. The solvent was removed from the filtrate by distillation, and then the remaining liquid was purified by silica gel column chromatography using hexane as a developing solvent to obtain the target product 4,5-di(n-pentyl)benzo[2,1-b:3,4-b'] dithiophene as an oily substance (41 mg). Analysis of the post-reaction solution by GC showed that the GC yield of the formed product was 89%. The obtained target product $^1$H-NMR and HRMS measurement results were as follows.

$^1$H-NMR (400 MHz, CDCl$_3$, ppm): δ7.46 (d, J=5.5 Hz, 2H), 7.37 (d, J=5.5 Hz, 2H), 3.02 (m, 4H), 1.70-1.62 (m, 4H), 1.53~1.37 (m, 8H) 0.93 (t, J=7.3 Hz, 6H).

HRMS (EI): m/z 330.1469 (Value obtained by measuring with C$_{20}$H$_{26}$S$_2$ was 330.1469.)

Example 6

Synthesis of 4,5-di(n-heptyl)benzo[2,1-b:3,4-b'] dithiophene)

The target product 4,5-di(n-heptyl)benzo[2,1-b:3,4-b'] dithiophene was obtained as an oily substance (58 mg) in the same manner as in Example 5, except that 8-hexadecene (53 mg (0.24 mmol)) was used instead of 6-dodecene. Analysis of the post-reaction solution by GC showed that the GC yield of the formed product was 99% or more. The obtained target product $^1$H-NMR and HRMS measurement results were as follows.

$^1$H-NMR 400 MHz, CDCl$_3$, ppm): δ7.46 (d, J=5.5 Hz, 2H), 7.36 (d, J=5.5 Hz, 2H), 3.01 (m, 4m), 1.70-1.61 (m, 4H), 1.52~1.45 (m, 4H) 1.41~1.25 (m, 12H), 0.90 (t, J=7.0 Hz, 6H).

HRMS (EI): m/z 386.2168 (Value obtained by measuring with C$_{24}$H$_{34}$S$_2$ was 386.2102.)

Example 7

Synthesis of 4,5-diphenylbenzo[2,1-b:3,4-b']dithiophene)

A two-necked 20 mL flask was charged with 3,3'-diiodo-2,2'-bithiophene (418 mg (1 mmol)), palladium(II) acetate (11 mg (0.05 mmol)), diphenylacetylene (214 mg (1.2 mmol)), N,N-dicyclohexylmethylamine (469 mg (2.4 mmol)), and N,N-dimethylformamide (2.5 mL). The contents of the reaction vessel were then purged with nitrogen, and a reaction was then carried out under stirring by heating at 130° C.

After 3 hours, the reaction solution was charged with diethyl ether (about 20 mL), and the resultant solution was then washed with water. Subsequently, the organic layer was dried over sodium sulfate, and filtered over Celite. The solvent was removed from the filtrate by distillation, and then the remaining liquid was purified by silica gel column chromatography using hexane as a developing solvent to obtain the target product 4,5-diphenylbenzo[2,1-b:3,4-b']dithiophene as a brown solid (134 mg). Analysis of the post-reaction solution by GC showed that the GC yield of the formed product was 64%. The obtained target product $^1$H-NMR and GC-MS measurement results were as follows.

$^1$H-NMR (400 MHz, CDCl$_3$, ppm): δ7.34 (d, J=5.5 Hz, 2H), 7.26-7.17 (m, 10H),7.16 (d, J=5.5H, 2H).

GC-MS (EI):m/z 342.

In Examples 1 to 7, it was confirmed that fused ring compounds represented by general formula (1) having various groups as the groups represented by R$^{11}$ and R$^{12}$ could be obtained. Further, from Examples 1 to 7, it was confirmed that a fused ring compound could be obtained in a high yield by using various kinds of amine as the base.

Example 8

Synthesis of 2,7-dibromo-4,5-di(n-propyl)benzo[2,1-b:3,4-b']dithiophene

A two-necked 20 mL flask was charged with 4,5-di(n-propyl)benzo[2,1-b:3,4-b']dithiophene (191.1 mg (0.70 mmol)), N-bromosuccinimide (261.6 mg (1.47 mmol)), and N,N-dimethylformamide (2.5 mL). The contents of the reaction vessel were purged with nitrogen, and a reaction was then carried out by stirring for 2.5 hours at room temperature.

The post-reaction solution was charged with diethyl ether (about 20 mL), and the resultant solution was then washed with water. Subsequently, the organic layer was dried over sodium sulfate, and then filtered. The solvent was removed from the filtrate by distillation, and then the resultant solid was recrystallized with hexane to obtain the target product 2,7-dibromo-4,5-di(n-propyl)benzo[2,1-b:3,4-b'] dithiophene as a white solid (214.5 mg, 70% yield). The obtained target product $^1$H-NMR and HRMS measurement results were as follows.

$^1$H-NMR (400 MHz, CDCl$_3$, ppm): δ7.40 (s, 2H), 2.91-2.86 (m, 4H), 1.67-1.60 (m, 4D, 1.06 (t, J=7.3 Hz, 6H).

HRMS (EI): m/z 429.9055 (Value obtained by measuring with C$_{16}$H$_{16}$Br$_2$S$_2$ was 429.9060.)

Example 9

Synthesis of 2,7-dibromo-4,5-di(n-pentyl)benzo[2,1-b:3,4-b']dithiophene)

A reaction was carried out in the same manner as in Example 8, except that 4,5-di(n-pentyl)benzo[2,1-b:3,4-b'] dithiophene (442.1 mg (1.34 mmol)) was used instead of 4,5-di(n-propyl)benzo[2,1-b:3,4-b']dithiophene. The post-reaction solution was charged with diethyl ether (about 20 mL), and the resultant solution was then washed with water. Subsequently, the organic layer was dried over sodium sulfate, and then filtered. The solvent was removed from the filtrate by distillation, and then the remaining liquid was purified by silica gel column chromatography using hexane as a developing solvent to obtain the target product 2,7-dibromo-4,5-di(n-pentyl)benzo[2,1-b:3,4-b']dithiophene as a white solid (124.9 mg, 59% yield). The obtained target product $^1$H-NMR and HRMS measurement results were as follows.

$^1$H-NMR (400 MHz, CDCl$_3$, ppm): δ7.39 (s, 2H), 2.94-2.85 (m, 4H), 1.64-1.54 (m, 4H), 1.50-1.32 (m, 8H), 0.93 (t, J=7.3 Hz, 6H).

HRMS (EI): m/z 485.9689 (Value obtained by measuring with C$_{20}$H$_{24}$Br$_2$S$_2$ was 485.9686.)

Example 10

Synthesis of 2,7-dibromo-4,5-di(n-heptyl)benzo[2,1-b:3,4-b']dithiophene

The target product 2,7-dibromo-4,5-di(n-heptyl)benzo[2,1-b:3,4-b']dithiophene was obtained as a white solid (242.0 mg, 69% yield) in the same manner as in Example 9, except that 4,5-di(n-heptyl)benzo[2,1-b:3,4-b']dithiophene (247.3 mg (0.64 mmol)) was used instead of 4,5-di(n-pentyl)benzo [2,1-b:3,4-b']dithiophene. The obtained target product $^1$H-NMR and HRMS measurement results were as follows.

$^1$H-NMR (400 MHz, CDCl$_3$, ppm): δ7.39 (s, 2H), 2.91-2.86 (m, 4H), 1.64-1.55 (m, 4H), 1.50-1.24 (m, 16H), 0.90 (t, J=7.3 Hz, 6H).

HRMS (EI): m/z 542.0314 (Value obtained by measuring with C$_{24}$H$_{32}$Br$_2$S$_2$ was 542.0312.)

Example 11

Synthesis of 2,7-diphenyl-4,5-di(n-propyl)benzo[2,1-b:3,4-b']dithiophene)

A two-necked 20 mL flask was charged with 2,7-dibromo-4,5-di(n-propyl)benzo[2,1-b:3,4-b']dithiophene (81.9 mg (0.19 mmol)), phenylboronic acid (92.7 mg (0.76 mmol)), palladium(II) acetate (2.1 mg, 0.01 mmol), potassium fluoride (88.3 mg (1.52 mmol)), di(t-butyl)-2-biphenylphosphine (5.7 mg (0.02 mmol), and toluene (2.5 mL). The contents of the reaction vessel were purged with nitrogen, and a reaction was then carried out by stirring for 3 hours at 100° C.

The post-reaction solution was charged with diethyl ether (about 20 mL), and the resultant solution was then washed with water. Subsequently, the organic layer was dried over sodium sulfate, and then filtered. The solvent was removed from the filtrate by distillation, and then the resultant solid was recrystallized with hexane and toluene to obtain the target product 2,7-diphenyl-4,5-di(n-propyl)benzo[2,1-b:3, 4-b']dithiophene as a yellow solid (64.5 mg, 80% yield). The obtained target product $^1$H-NMR and HRMS measurement results were as follows.

$^1$H-NMR (400MHz, CDCl$_3$, ppm): δ7.77-7.74 (m, 4H), 7.65 (s, 2H), 7.47-7.42 (m, 4H), 7.37-7.32 (m, 2H), 3.05-3.00 (m, 4H), 1.78-1.69 (m, 4H), 1.11 (t, J=7.3 Hz, 6H).

HRMS (EI): m/z 426.1480 (Value obtained by measuring with C$_{28}$H$_{26}$S$_2$ was 426.1480.)

Example 12

Synthesis of 2,7-diphenyl-4,5-di(n-pentyl)benzo[2,1-b:3,4-b']dithiophene

A reaction was carried out in the same manner as in Example 11, except that 2,7-dibromo-4,5-di(n-pentyl)benzo[2,1-b:3,4-b']dithiophene (124.9 mg (0.26 mmol)) was used instead of 2,7-dibromo-4,5-di(n-propyl)benzo[2,1-b:3,4-b']dithiophene. The post-reaction solution was charged with diethyl ether (about 20 mL), and the resultant solution was then washed with water. Subsequently, the organic layer was dried over sodium sulfate, and then filtered. The solvent was removed from the filtrate by distillation, and then the remaining solid was purified by thin-layer column chromatography using hexane as a developing solvent to obtain the target product 2,7-diphenyl-4,5-di(n-pentyl)benzo[2,1-b:3,4-b']dithiophene as a yellow solid (83.8 mg, 67% yield). The obtained target product $^1$H-NMR and HRMS measurement results were as follows.

$^1$H-NMR (400 MHz, CDCl$_3$, ppm): δ7.77-7.74 (m, 4H), 7.66 (s, 2H), 7.47-7.42 (m, 4H), 7.37-7.32 (m, 2H), 3.05-3.00 (m, 4H), 1.79-1.68 (m, 4H), 1.55-1.40 (m, 8H), 0.95 (t, J=7.3Hz, 6H).

HRMS (EI): m/z 482.2097 (Value obtained by measuring with C$_{32}$H$_{34}$S$_2$ was 482.2102.)

Example 13

Synthesis of 2,7-diphenyl-4,5-di(n-heptyl)benzo[2,1-b:3,4-b']dithiophene

The target product 2,7-diphenyl-4,5-di(n-heptyl)benzo[2,1-b:3,4-b']dithiophene was obtained as a yellow solid (54.5 mg, 42% yield) in the same manner as in Example 12, except that 2,7-dibromo-4,5-di(n-heptyl)benzo[2,1-b:3,4-b']dithiophene (128.2 mg (0.24 mmol)) was used instead of 2,7-dibromo-4,5-di(n-pentyl)benzo[2,1-b:3,4-b']dithiophene. The obtained target product $^1$H-NMR and HRMS measurement results were as follows.

$^1$H-NMR (400 MHz, CDCl$_3$, ppm): δ7.77-7.71 (m, 4H), 7.63 (s, 2H), 7.46-7.40 (m, 4H), 7.36-7.30 (m, 2H), 3.05-2.97 (m, 4H), 1.74-1.63 (m, 4H), 1.56-1.47 (m, 4H), 1.46-1.19 (m, 12H), 0.91 (t, J=6.9 Hz, 6H).

HRMS (EI): m/z 538.2722 (Value obtained by measuring with C$_{36}$H$_{42}$S$_2$ was 538.2728.)

Example 14

Synthesis of 2,7-di(2-naphthyl)-4,5-di(n-pentyl)benzo[2,1-b:3,4-b']dithiophene

The target product 2,7-di(2-naphthyl)-4,5-di(n-pentyl)benzo[2,1-b:3,4-b']dithiophene was obtained as a yellow solid (72.0 mg, 62% yield) in the same manner as in Example 12, except that 2-naphthylboronic acid (137.6 mg (0.80 mmol)) was used instead of phenylboronic acid. The obtained target product $^1$H-NMR and HRMS measurement results were as follows.

$^1$H-NMR (400 MHz, CDCl$_3$, ppm): δ8.15 (s, 2H), 7.92-7.81 (m, 8H), 7.75 (s, 2H), 7.54-7.45 (m, 4H), 3.08-3.03 (m, 4H), 1.78-1.69 (m, 4H), 1.58-1.40 (m, 8H), 0.97 (t, J=7.3Hz, 6H).

HRMS (EI): m/z 582.2423 (Value obtained by measuring with C$_{40}$H$_{38}$S$_2$ was 582.2415.)

Example 15

Synthesis of 2,7-di(2-naphthyl)-4,5-di(n-heptyl)benzo[2,1-b:3,4-b']dithiophene

The target product 2,7-di(2-naphthyl)-4,5-di(n-heptyl)benzo[2,1-b:3,4-b']dithiophene was obtained as a yellow solid (96.6 mg, 94% yield) in the same manner as in Example 11, except that 2-naphthylboronic acid (111.8 mg (0.65 mmol)) was used instead of phenylboronic acid, and 2,7-dibromo-4,5-di(n-heptyl)benzo[2,1-b:3,4-b']dithiophene (89.1 mg (0.16 mmol)) was used instead of 2,7-dibromo-4,5-di(n-propyl)benzo[2,1-b:3,4-b']dithiophene. The obtained target product $^1$H-NMR and HRMS measurement results were as follows.

$^1$H-NMR (400 MHz, CDCl$_3$, ppm): δ8.19 (s, 2H), 7.93-7.83 (m, 8H), 7.78 (s, 2H), 7.55-7.47 (m, 4H), 3.11-3.03 (m, 4H), 1.79-1.69 (m, 4H), 1.61-1.28 (m, 16H), 0.92 (t, J=6.9 Hz, 6H).

HRMS (EI): m/z 638.3031 (Value obtained by measuring with C$_{44}$H$_{46}$S$_2$ was 638.3041.)

Example 16

Synthesis of 2,7-di(4-biphenyl)-4,5-di(n-pentyl)benzo[2,1-b:3,4-b']dithiophene

The target product 2,7-di(4-biphenyl)-4,5-di(n-pentyl)benzo[2,1-b:3,4-b']dithiophene was obtained as a yellow solid (122.5 mg, 96% yield) in the same manner as in Example 14, except that 4-biphenylboronic acid (158.6 mg (0.80 mmol)) was used instead of 2-naphthylboronic acid. The obtained target product $^1$H-NMR and HRMS measurement results were as follows.

$^1$H-NMR (400 MHz, CDCl$_3$, ppm): δ7.84-7.80 (m, 4H), 7.70-7.63 (m, 8H), 7.69 (s, 2H), 7.50-7.45 (m, 4H), 7.40-7.35 (m, 2H), 3.07-3.02 (m, 4H), 1.77-1.68 (m, 4H), 1.56-1.41 (m, 8H), 0.97 (t, J=7.3 Hz, 6H).

HRMS (EI): m/z 634.2720 (Value obtained by measuring with C44H$_{42}$S$_2$ was 634.2728.)

Example 17

Synthesis of 2,7-di(4-biphenyl)-4,5-di(n-heptyl)benzo[2,1-b:3,4-b']dithiophene

The target product 2,7-di(4-biphenyl)-4,5-di(n-heptyl)benzo[2,1-b:3,4-b']dithiophene was obtained as a yellow solid (56.4 mg, 63% yield) in the same manner as in Example 15, except that 4-biphenylboronic acid (103.0 mg (0.52 mmol)) was used instead of 2-naphthylboronic acid. The obtained target product $^1$H-NMR and HRMS measurement results were as follows.

$^1$H-NMR (400 MHz, CDCl$_3$, ppm): δ7.84-7.80 (m, 4H), 7.71-7.63 (m, 8H), 7.69 (s, 2H), 7.50-7.44 (m, 4H), 7.41-7.35 (m, 2H), 3.08-3.02 (m, 4H), 1.76-1.66 (m, 4H), 1.58-1.25 (m, 16H), 0.92 (t, J=6.9 Hz, 6H).

HRMS (EI): m/z 690.3362 (Value obtained by measuring with $C_{48}H_{50}S_2$ was 690.3354.)

Example 18

Synthesis of 2,7-diphenyl-4,5-di(n-pentyl)benzo[2,1-b:3,4-b']dithiophene

A two-necked 20 mL flask was charged with 4,5-di(n-pentyl)benzo[2,1-b:3,4-b']dithiophene (172.4 mg (0.52 mmol)), bromobenzene (244.9 mg (1.56 mmol)), palladium (II) acetate (11.7 mg (0.05 mmol)), cesium carbonate (407.3 mg (1.25 mmol)), di(t-butyl)-2-biphenylphosphine (29.8 mg (0.1 mmol), and N,N-dimethylformamide (2.5 mL). The contents of the reaction vessel were purged with nitrogen, and a reaction was then carried out by stirring for 17 hours at 150° C.

The post-reaction solution was charged with diethyl ether (about 20 mL), and the resultant solution was then washed with water. Subsequently, the organic layer was dried over sodium sulfate, and then filtered. The solvent was removed from the filtrate by distillation, and then the resultant solid was recrystallized with hexane and toluene to obtain the target product 2,7-diphenyl-4,5-di(n-pentyl)benzo[2,1-b:3,4-b']dithiophene as a yellow solid (94.0 mg, 37% yield).

Example 19

Synthesis of 2,7-di(2-thienyl)-4,5-di(n-heptyl)benzo[2,1-b:3,4-b']dithiophene

A two-necked 30 mL flask was charged with 2,7-dibromo-4,5-di(n-heptyl)benzo[2,1-b:3,4-b']dithiophene (163.3 mg (0.30 mmol)), tributyl(2-thienyl)tin (223.9 mg (0.6 mmol)), tetrakis(triphenylphosphine)palladium (17.3 mg (0.015 mmol), N,N-dimethylformamide (2.5 mL), and toluene (2.5 mL). The contents of the reaction vessel were purged with nitrogen, and a reaction was then carried out by stirring for 24 hours at 85° C.

The post-reaction solution was charged with methylene chloride (about 20 mL), and the resultant solution was then washed with water. Subsequently, the organic layer was dried over sodium sulfate, and then filtered through filter paper. The solvent was removed from the filtrate by distillation, and then the resultant solid was dissolved in toluene. The resultant solution was purified by silica gel column chromatography using hexane as a developing solvent, and the resultant product was recrystallized with hexane to obtain the target product 2,7-di(2-thienyl)-4,5-di(n-heptyl)benzo[2,1-b:3,4-b']dithiophene as a yellow-white solid (89.2 mg, 54% yield). The obtained target product $^1$H-NMR measurement results were as follows.

$^1$H-NMR (400 MHz, $CDCl_3$, ppm): δ7.46 (s, 2M),7.31-7.27 (m, 4H), 7.07-7.04 (dd, J=5.2, 3.6 Hz, 2H), 2.99-2.92 (m, 4H), 1.68-1.60 (m, 4H), 1.54-1.27 (m, 16H), 0.92 (t, J=7.3 Hz, 6H).

[Polymer Production]

Example 20

Synthesis of poly(4,5-di(n-heptyl)benzo[2,1-b:3,4-b']dithiophene

A two-necked 20 mL flask was charged with 2,7-dibromo-4,5-di(n-heptyl)benzo[2,1-b:3,4-b']dithiophene (108.9 mg (0.20 mmol)), Ni(COD)$_2$ (66.0 mg (0.24 mmol)), 1,5-cyclooctadiene (21.6 mg (0.20 mmol)), bipyridyl (37.5 mg (0.24 mmol)), and N,N-dimethylformamide (2.5 mL). The contents of the reaction vessel were purged with nitrogen, and a reaction was then carried out by stirring for 24 hours at 60° C.

The post-reaction solution was charged with toluene (about 20 mL), and the resultant solution was then washed with water. Subsequently, the organic layer was dried over sodium sulfate, and then filtered through pleated filter paper. The solvent was removed from the filtrate by distillation, and then the resultant solid was purified by silica gel column chromatography using hexane and toluene (7:3) as a developing solvent. The resultant liquid was charged with ethanol to obtain the target product poly(4,5-di(n-heptyl)benzo[2,1-b:3,4-b']dithiophene) as an auburn solid (36.4 mg). The obtained polymer will be referred to as "Polymer A".

Example 21

Synthesis of poly(4,5-di(n-heptyl)benzo[2,1-b:3,4-b']dithiophene)

A two-necked 100 mL flask was charged with 4,5-di(n-heptyl)benzo[2,1-b:3,4-b']dithiophene (223.4 mg (0.58 mmol)), iron(III) chloride (1844.5 mg (11.6 mmol)), and dichloromethane (20 mL). The contents of the reaction vessel were purged with nitrogen, and a reaction was then carried out by stirring for 20 hours at room temperature.

The post-reaction solution was charged with an aqueous solution of hydrazine and toluene (about 20 mL), and the resultant solution was then washed with water. Subsequently, the organic layer was dried over sodium sulfate, and then filtered. The solvent was removed from the filtrate by distillation, and then the resultant product was purified by silica gel column chromatography using hexane and toluene (7:3) as a developing solvent. The resultant liquid was charged with ethanol to obtain the target product poly(4,5-di(n-heptyl)benzo[2,1-b:3,4-b']dithiophene) as an auburn solid (37.3 mg). The obtained polymer will be referred to as "Polymer B".

Example 22

Synthesis of poly(4,5-di(n-heptyl)benzo[2,1-b:3,4-b']dithiophene)

A two-necked 20 mL flask was charged with 4,5-di(n-heptyl)benzo[2,1-b:3,4-b']dithiophene (119.3 mg (0.31 mmol)), iron(III) chloride (110.6 mg (0.68 mmol)), and chlorobenzene (5.5 mL). A reaction was then carried out by stirring for 36 hours at 65° C. in an air atmosphere.

The post-reaction solution was charged with an aqueous solution of hydrazine and with toluene (about 20 mL), and the resultant solution was then washed with water. Subsequently, the organic layer was filtered through filter paper. The solids which adhered to the filter paper were recovered by dissolving in chloroform. The solvent was removed by distillation, and then the resultant solid was washed with ethanol to obtain the target product poly(4,5-di(n-heptyl)benzo[2,1-b:3,4-b']dithiophene) as an auburn solid (41.5 mg). The obtained polymer will be referred to as "Polymer C".

Example 23

Synthesis of poly(9,9-dioctylfluorene-co-4,5-di(n-heptyl)benzo[2,1-b:3,4-b']dithiophene)

A 50 mL carousel test tube which had been purged with nitrogen was charged with 2,7-bis(ethylboronate)-9,9-dioctylfluorene (0.26 mmol), 2,7-dibromo-4,5-di(n-heptyl)benzo[2,1-b:3,4-b']dithiophene (0.26 mmol)), and dichlorobis(triphenylphosphine)palladium (0.19 µmol). Then, 4 mL of toluene which had been bubbled in advance with nitrogen for 30 minutes was charged into the test tube, and the resultant solution was stirred to completely dissolve.

Next, the solution was charged with Aliquat 336 (0.07 mmol), and the test tube was sealed. While increasing the temperature to 105° C., an aqueous solution of sodium carbonate (2 mol/L, 0.48 mL) was added dropwise through a septum by a syringe and the resultant solution was stirred while heating for 5 hours. Further, phenylboronic acid (4.2 mg) was dissolved in THF, and this solution was charged into the test tube. The resultant solution was then stirred while heating for 5 hours at 105° C. The resultant solution was cooled to 90° C., and then 0.1 g of sodium N,N-diethyldithiocarbamate trihydrate dissolved in deionized water was charged thereto. The solution was then stirred while heating for 3 hours at 90° C.

Then, the stirring was stopped, and the aqueous layer was removed. The organic layer was washed 3 times with 4 mL of 60° C. deionized water, then washed 3 times with 4 mL of 3% acetic acid, and then again washed 3 times with 60° C. deionized water. Then, the resultant mixture was purified by chromatography using silica gel and a neutral alumina column, and then reprecipitated with 60 mL of methanol to obtain the target polymer. The molecular weight of the obtained polymer in terms of polystyrene was $1.0 \times 10^5$. The obtained polymer will be referred to as "Polymer D".

Example 24

Synthesis of poly(2,2'-bithiophene-co-4,5-di(n-heptyl)benzo[2,1-b:3,4-b']dithiophene)

A 50 mL Schlenk flask which had been purged with nitrogen was charged with 5,5-bis(trimethylstamyl)-2,2'-bithiophene (0.44 mmol), 2,7-dibromo-4,5-di(n-heptyl)benzo[2,1-b:3,4-b']dithiophene (0.37 mmol)), and dichlorobis(triphenylphosphine)palladium (0.97 µmol). Then, the resultant solution was charged with 3 mL of DMF. The temperature of the solution was increased to 150° C., and the solution was stirred for 24 hours. Next, the solution was charged with 2 mL of THF, and the resultant solution was stirred for a further 48 hours. The resultant solution was cooled to room temperature, and then the solution was reprecipitated with 50 mL of a methanol/water mixed solution (1:1) to obtain the target polymer. The molecular weight of the obtained polymer in terms of polystyrene was $4.1 \times 10^3$. The obtained polymer will be referred to as "Polymer E".

[Production and Evaluation of an Organic Thin Film Device]

Example 25

Organic Thin Film Transistor Production and Evaluation of its Characteristics 5 mg of Polymer D was weighed, and 1 g of chloroform was added thereto to prepare a 0.5 wt % chloroform solution. This solution was then filtered through a 0.2 µm membrane filter made of Teflon® to form a coating solution.

Next, on the surface of a heavily doped n-type silicon substrate which will act as a gate electrode, a substrate formed with a 200 nm thermally oxidized silicon oxide film which will act as an insulating layer was subjected to ultrasonic cleaning with an alkali detergent, ultrapure water, and acetone, and then the surface was cleaned by ozone UV irradiation. Hexamethyldisilazane (HMDS, manufactured by Aldrich) was added dropwise onto this cleaned substrate, which was then spun at 2000 rpm to treat the substrate surface with HMDS. The above-described solution of Polymer D in chloroform (coating solution) was added dropwise onto this surface-treated substrate, which was then spun at 1000 rpm to form a thin film of Polymer D.

Then, on the thin film of Polymer D, a Pt/Au electrode was vapor-deposited to 2 nm/50 nm by vacuum deposition using a metal mask to form a source electrode and a drain electrode having a channel width of 2 mm and a channel length of 20 µm, whereby an organic thin film transistor was obtained.

In the obtained thin film transistor, when the transistor characteristics were measured by changing the gate voltage $V_G$ and the voltage $V_{SD}$ between the source and the drain in a vacuum, good Id-Vg characteristics were obtained. Further, a current in which the drain current Id=$1.5 \times 10^{-7}$ A was flowed at Vg=−60 V and Vd=−60 V. The mobility at this point was $1.3 \times 10^{-3}$ cm$^2$/Vs, the on/off ratio was $10^4$, and the threshold voltage at which the current entered was −27 V.

Example 26

Organic Thin Film Transistor Production and Evaluation of its Characteristics

An organic thin film transistor is produced in the same manner as in Example 25, except that Polymer D is replaced with Polymer A. When transistor characteristics are measured by changing the gate voltage $V_G$ and the voltage $V_{SD}$ between the source and the drain in a vacuum, good Id-Vg characteristics are obtained.

Example 27

Organic Thin Film Transistor Production and Evaluation of its Characteristics

An organic thin film transistor is produced in the same manner as in Example 25, except that Polymer C is used instead of Polymer D. When the transistor characteristics are measured by changing the gate voltage $V_G$ and the voltage $V_{SD}$ between the source and the drain in a vacuum, good Id-Vg characteristics are obtained Example 28

Organic Thin Film Transistor Production and Evaluation of its Characteristics

An organic thin film transistor was produced in the same manner as in Example 25, except that Polymer E was used instead of Polymer D. When the transistor characteristics were measured by changing the gate voltage $V_G$ and the voltage $V_{SD}$ between the source and the drain in a vacuum, good Id-Vg characteristics were obtained. Then, a current in which the drain current Id=$2.2 \times 10^{-8}$ A was flowed at Vg=−60 V and Vd=−60 V. The mobility at this point was $1.6 \times 10^{-5}$ cm$^2$/Vs, the on/off ratio was $10^2$, and the threshold voltage at which the current flowed was −5 V.

The invention claimed is:
1. A fused ring compound represented by the following general formula (1),

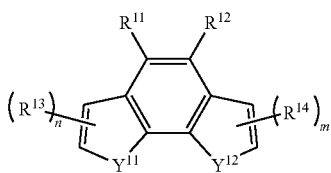

(1)

wherein $R^{11}$ and $R^{12}$ each independently represent an ethyl group, an n-propyl group, an iso-propyl group, an n-butyl group, an iso-butyl group, a tert-butyl group, a pentyl group, a hexyl group, a heptyl group, an octyl group, a nonyl group, a decyl group, a lauryl group, a cyclopropyl group, a cyclopentyl group, a cyclohexyl group, a cycloheptyl group, a cyclooctyl group, a cyclononyl group, or a cyclododecyl group; $R^{13}$ and $R^{14}$ each independently represent a monovalent group, and n and m each independently denote an integer of 0 to 2, provided that when a plurality of both $R^{13}$ and $R^{14}$ are present, such groups may be the same or different; and $Y^{11}$ and $Y^{12}$ are each independently a divalent group represented by the following general formula (2a),

(2a)

2. The fused ring compound according to claim 1, wherein $R^{11}$ and $R^{12}$ are each independently an ethyl group, an n-propyl group, an iso-propyl group, an n-butyl group, an iso-butyl group, a tert-butyl group, a pentyl group, a hexyl group, a heptyl group, an octyl group, a nonyl group, a decyl group, a cyclopropyl group, a cyclopentyl group, a cyclohexyl group, a cycloheptyl group, a cyclooctyl group, or a cyclononyl group.

3. An organic thin film, comprising the fused ring compound according to claim 1.

* * * * *